United States Patent
Kamat

(10) Patent No.: US 8,574,283 B1
(45) Date of Patent: Nov. 5, 2013

(54) DEPLOYMENT OF STENTS WITHIN BIFURCATED VESSELS

(76) Inventor: Suraj Govind Kamat, Alice, TX (US)

( * ) Notice: Subject to any disclaimer, the term of this patent is extended or adjusted under 35 U.S.C. 154(b) by 0 days.

(21) Appl. No.: 13/473,892

(22) Filed: May 17, 2012

Related U.S. Application Data

(60) Provisional application No. 61/528,968, filed on Aug. 30, 2011.

(51) Int. Cl.
*A61F 2/06* (2013.01)
*A61M 29/00* (2006.01)

(52) U.S. Cl.
USPC .......... 623/1.11; 623/1.35; 606/191; 606/194

(58) Field of Classification Search
USPC ............. 623/1.35, 1.11, 901, 909, 1.23, 2.11; 606/191, 194, 108; 29/283.5, 516
See application file for complete search history.

(56) References Cited

U.S. PATENT DOCUMENTS

| | | | | |
|---|---|---|---|---|
| 5,409,495 A * | 4/1995 | Osborn | .................. | 623/1.11 |
| 5,749,825 A | 5/1998 | Fischell et al. | | |
| 5,961,548 A * | 10/1999 | Shmulewitz | ................. | 623/1.35 |
| 6,048,361 A | 4/2000 | Von Oepen | | |
| 6,221,098 B1 * | 4/2001 | Wilson et al. | ................. | 623/1.11 |
| 6,325,823 B1 * | 12/2001 | Horzewski et al. | .......... | 623/1.16 |
| 6,602,279 B1 * | 8/2003 | Nicholas | ...................... | 623/1.11 |
| 6,682,553 B1 * | 1/2004 | Webler, Jr. | .................... | 623/1.11 |
| 6,682,556 B1 | 1/2004 | Ischinger | | |
| 6,692,483 B2 | 2/2004 | Vardi et al. | | |
| 6,896,694 B1 * | 5/2005 | Filho et al. | ................... | 623/1.11 |
| 7,686,845 B2 | 3/2010 | Sequin et al. | | |
| 7,686,846 B2 | 3/2010 | Laborde et al. | | |
| 7,763,198 B2 * | 7/2010 | Knott et al. | .................... | 264/249 |
| 7,992,273 B2 * | 8/2011 | Austin | ......................... | 29/283.5 |
| 2001/0049548 A1 | 12/2001 | Vardi et al. | | |
| 2002/0138126 A1 * | 9/2002 | Camrud et al. | .............. | 623/1.11 |
| 2002/0147491 A1 | 10/2002 | Khan et al. | | |
| 2003/0028233 A1 | 2/2003 | Vardi et al. | | |
| 2003/0055483 A1 | 3/2003 | Gumm | | |
| 2004/0143286 A1 * | 7/2004 | Johnson et al. | ............... | 606/194 |
| 2005/0033404 A1 * | 2/2005 | Eidenschink | ................ | 623/1.11 |
| 2005/0038494 A1 * | 2/2005 | Eidenschink | ................ | 623/1.11 |

(Continued)

OTHER PUBLICATIONS

Safian, Robert D., MD et al., "The Manual of Interventional Cardiology," Third Edition, 2001, Chapter 10, pp. 221-235, Physicians' Press, Royal Oak, Michigan.

(Continued)

*Primary Examiner* — Gary Jackson
*Assistant Examiner* — Richard Louis
(74) *Attorney, Agent, or Firm* — Fogarty, L.L.C.

(57) ABSTRACT

Systems and methods for deploying stents within bifurcated vessels in a true pantaloons configuration (Kamat technique) are disclosed. A device including a balloon catheter and a stent surrounding the catheter is inserted into a bifurcated blood vessel. The catheter includes a first lumen configured to accept a first guide wire, which exits the device at a distal end. The device is advanced within a main branch using the first guide wire until it reaches the carina, thus causing the second guide wire to enter a second side branch. The second wire exits the device at a tapered edge of the catheter from under the stent. The stent may then be deployed within the main branch. The stent may then be splayed across the carina with kissing balloons and the procedure may be completed with the kissing balloon deployment of two stents accurately at the carina in each side branch.

6 Claims, 23 Drawing Sheets

(56) References Cited

U.S. PATENT DOCUMENTS

| | | | |
|---|---|---|---|
| 2005/0119720 A1* | 6/2005 | Gale et al. | 623/1.11 |
| 2005/0209673 A1 | 9/2005 | Shaked | |
| 2006/0259116 A1* | 11/2006 | Feld et al. | 623/1.11 |
| 2006/0271090 A1* | 11/2006 | Shaked et al. | 606/192 |
| 2007/0168020 A1* | 7/2007 | Brucker et al. | 623/1.35 |
| 2007/0270933 A1* | 11/2007 | Von Oepen et al. | 623/1.11 |
| 2007/0276468 A1* | 11/2007 | Holzer et al. | 623/1.35 |
| 2007/0282419 A1* | 12/2007 | Hilaire et al. | 623/1.11 |
| 2007/0288082 A1* | 12/2007 | Williams | 623/1.11 |
| 2008/0046072 A1* | 2/2008 | Laborde et al. | 623/1.34 |
| 2010/0241212 A1* | 9/2010 | Shaked et al. | 623/1.11 |
| 2011/0106246 A1* | 5/2011 | Malewicz et al. | 623/2.11 |
| 2011/0160833 A1* | 6/2011 | Gonzalez et al. | 623/1.11 |

OTHER PUBLICATIONS

Kwan, Tak W., MD et al., "Tips and Tricks for Stenting of Bifurcation Coronary Lesions," The Journal of Invasive Cardiology, Sep. 2010, pp. 440-444, vol. 22/No. 9, HMP Communications, LLC, Malvern, Pennsylvania.

Aminian, Adel, MD et al., "Small Balloon Inflation Over a Jailed Wire as a Bailout Technique in a Case of Abrupt Side Branch Occlusion During Provisional Stenting," The Journal of Invasive Cardiology, Sep. 2010, pp. 449-452, vol. 22/No. 9, HMP Communications, LLC, Malvern, Pennsylvania.

Agostoni, Pierfrancesco, MD et al., "Optical Coherence Tomography Assessment of a Coronary Bare Cobalt Chromium Stent Deformed by the Removal of an Entrapped 'Jailed' Guidewire," The Journal of Invasive Cardiology, Sep. 2010, pp. 453-455, vol. 22/No. 9, HMP Communications, LLC, Malvern, Pennsylvania.

Latib, Azeem et al., "Bifurcation stenting: current strategies and new devices," Heart, Sep. 23, 2008, pp. 495-504, vol. 95, BMJ Publishing Group Ltd.

Chen, Shao-Liang et al., "Dedicated Bifurcation Stents Strategy," Interventional Cardiology, 2009, pp. 70-72, vol. 4, Touch Briefings.

Abizaid, Alexandre et al., "Bifurcated stents: giving to Caeser what is Caeser's," EuroIntervention, 2007, pp. 518-525, vol. 2, Euro PCR.

* cited by examiner

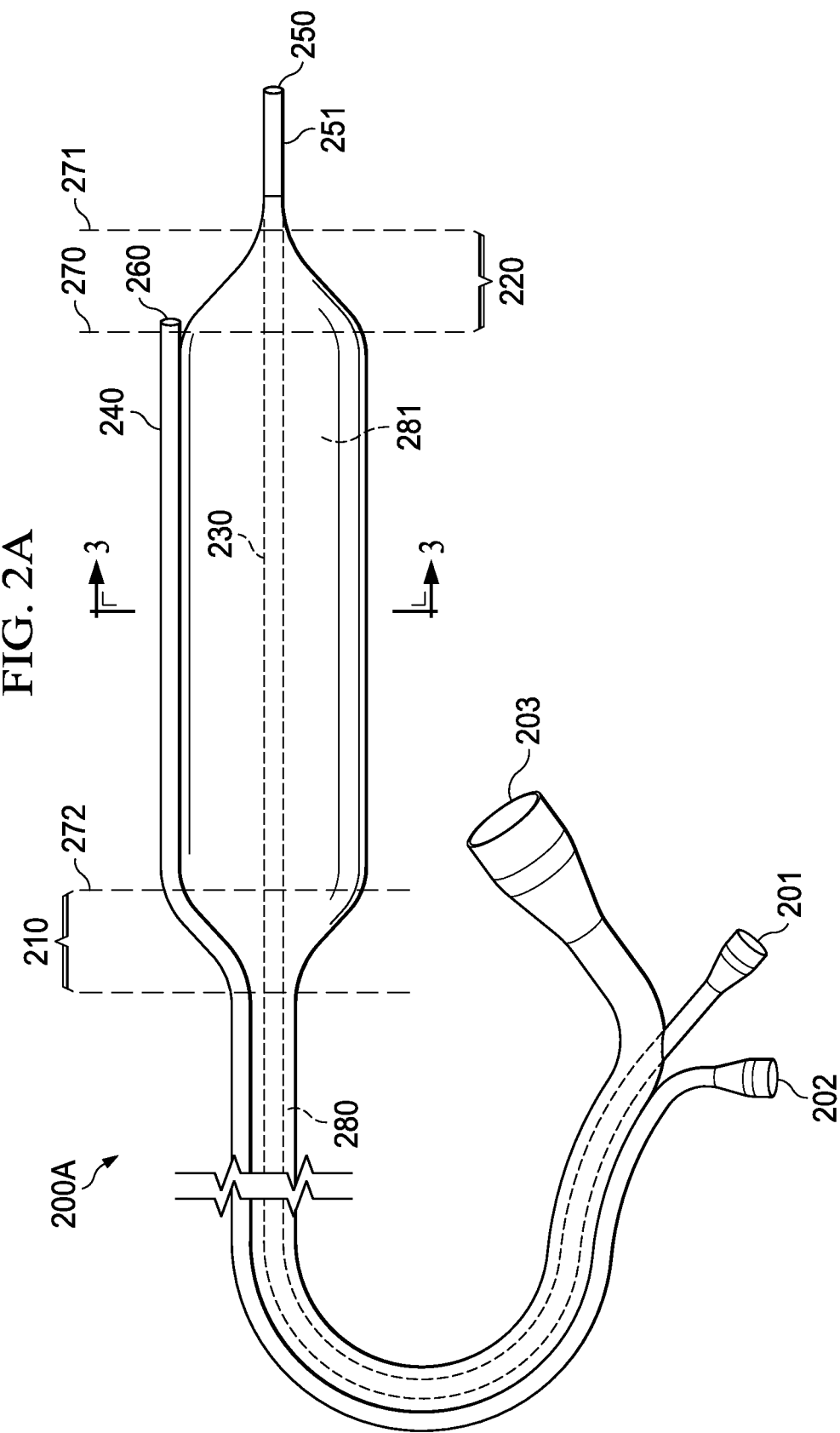

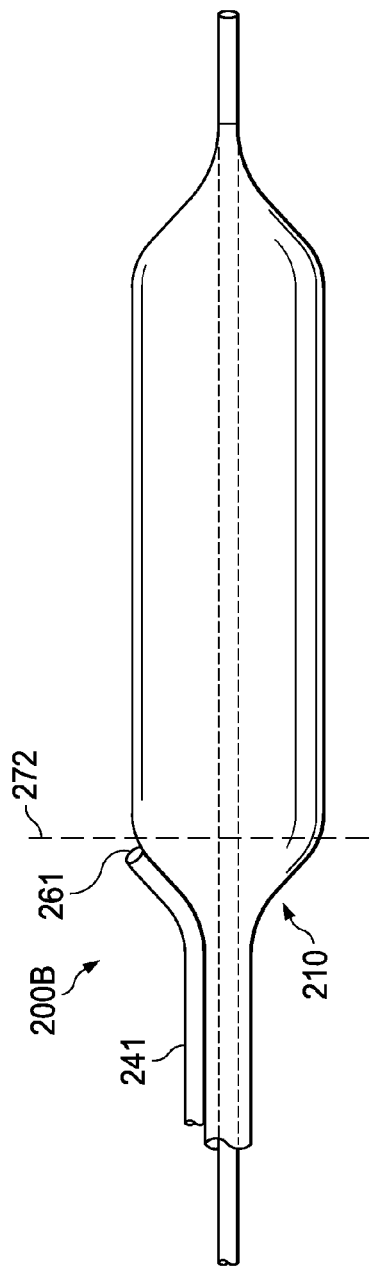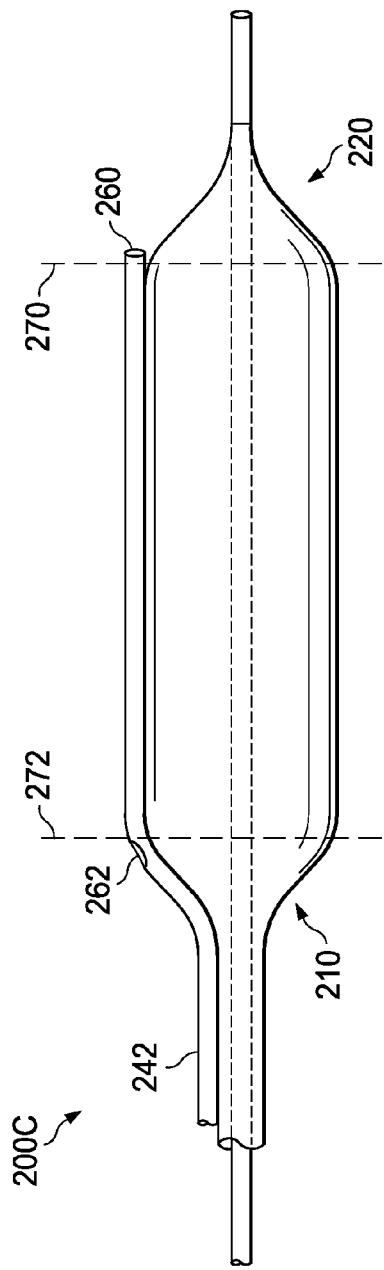

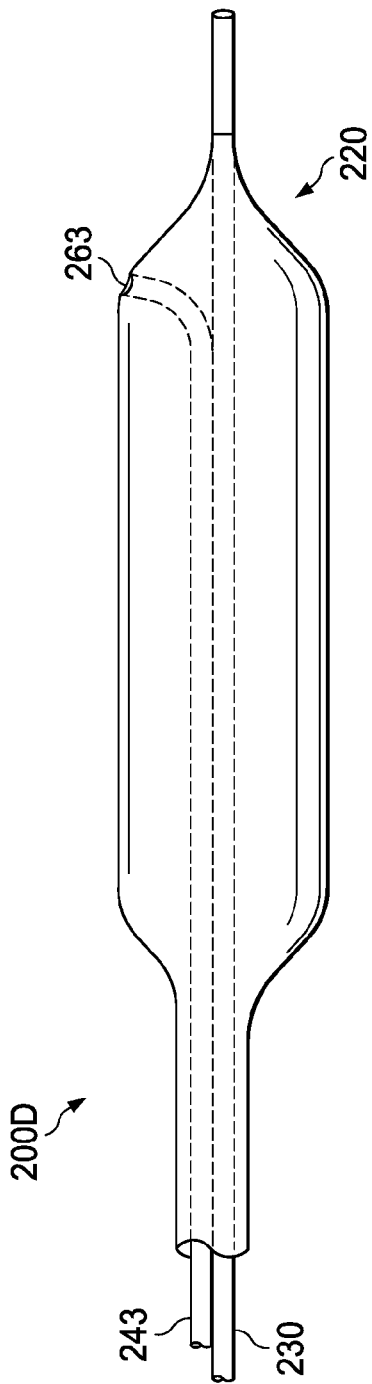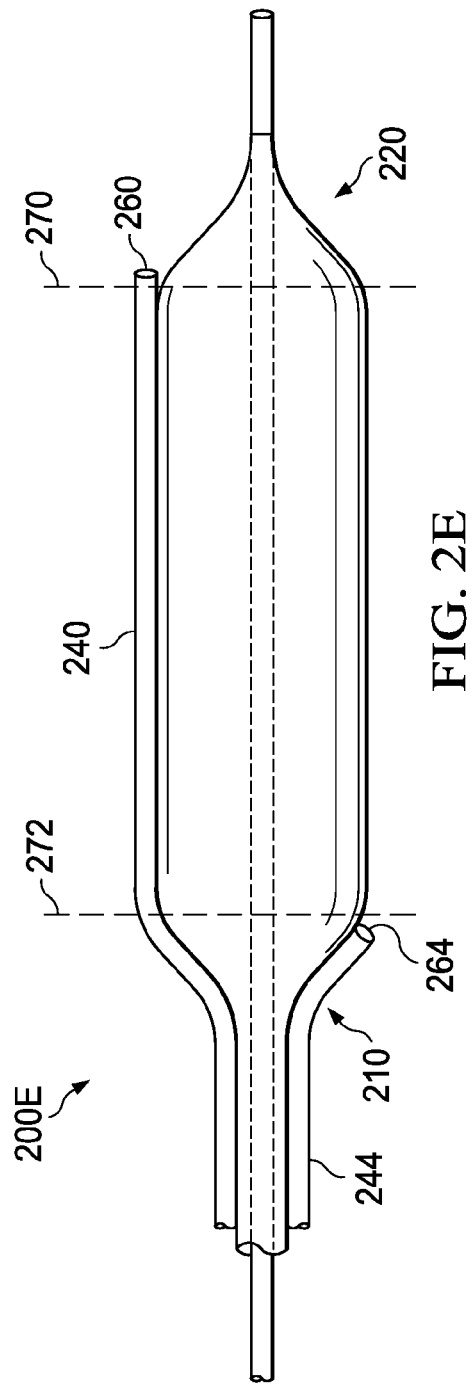

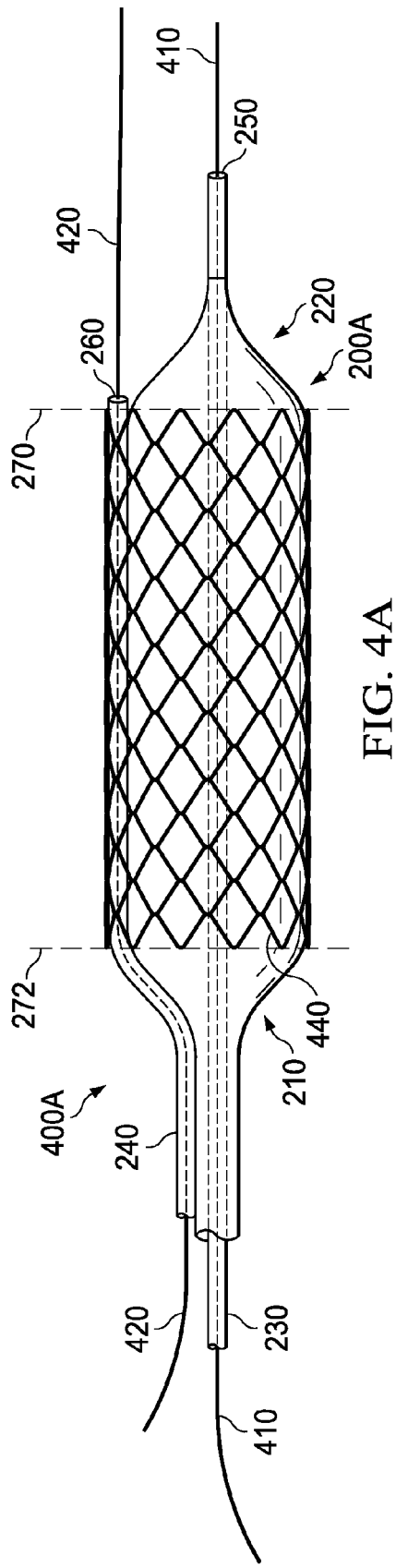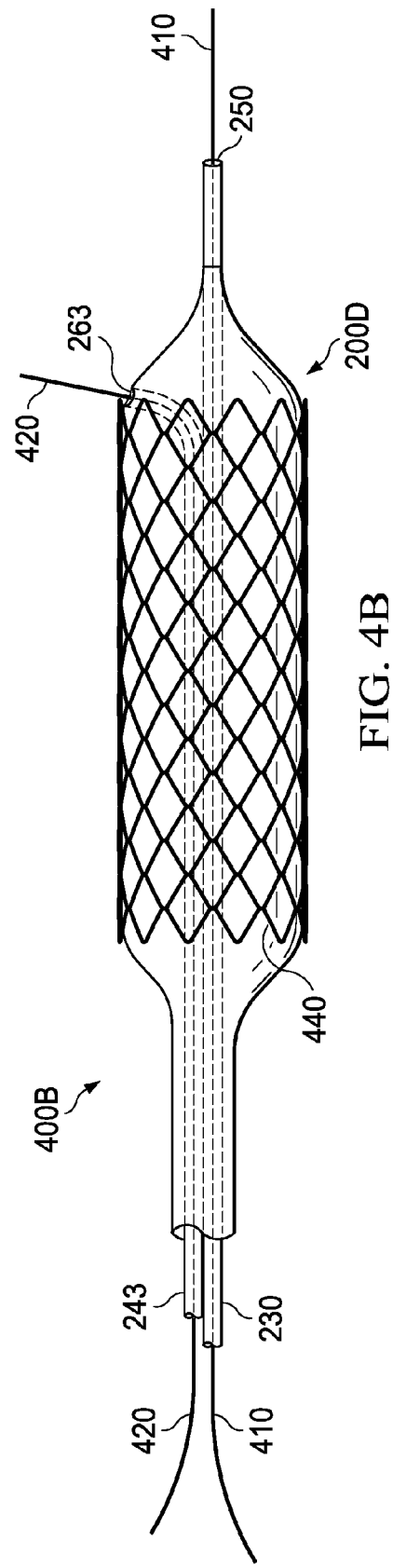

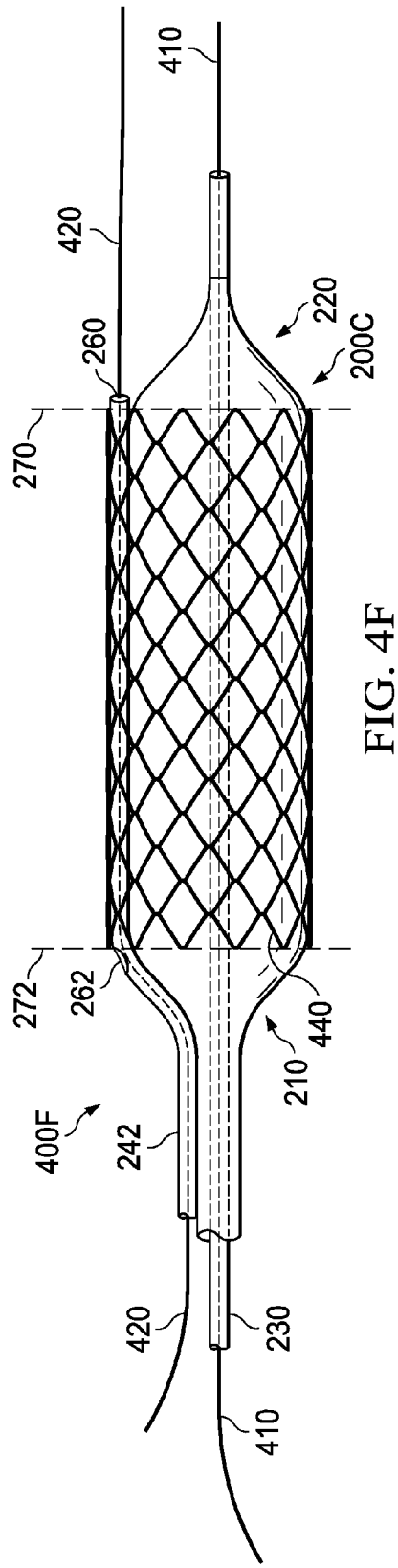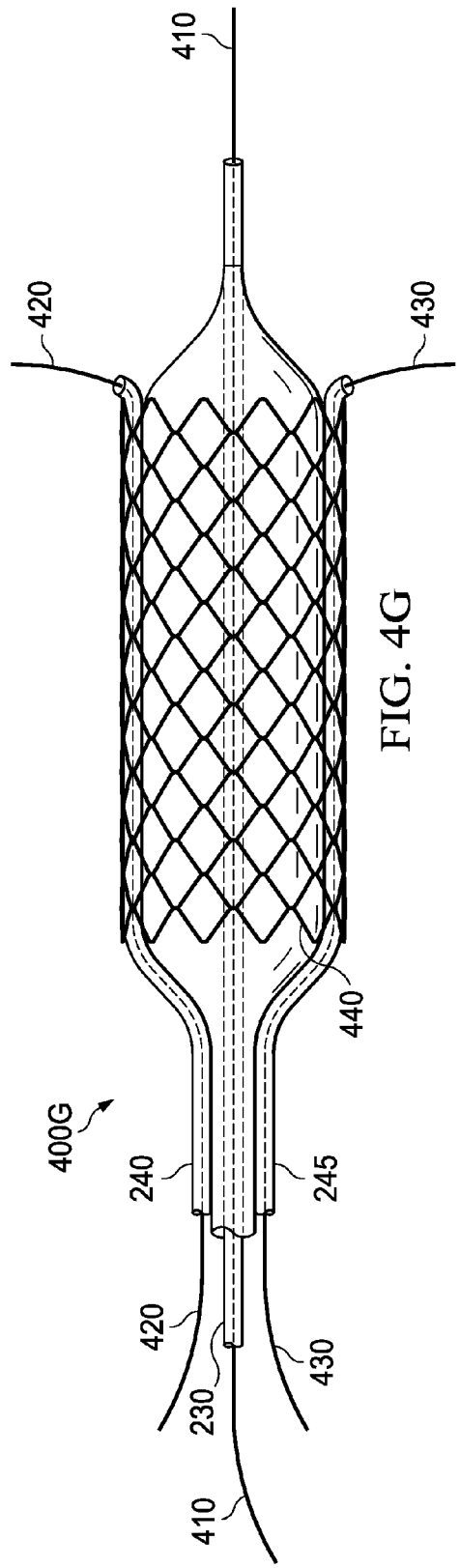

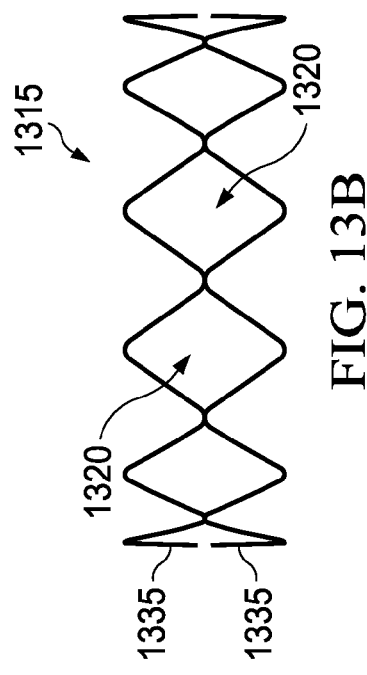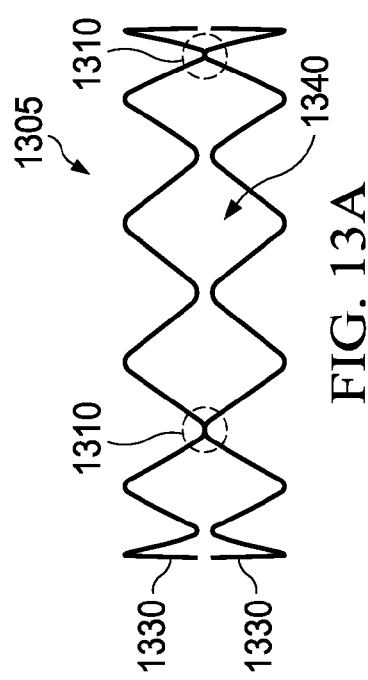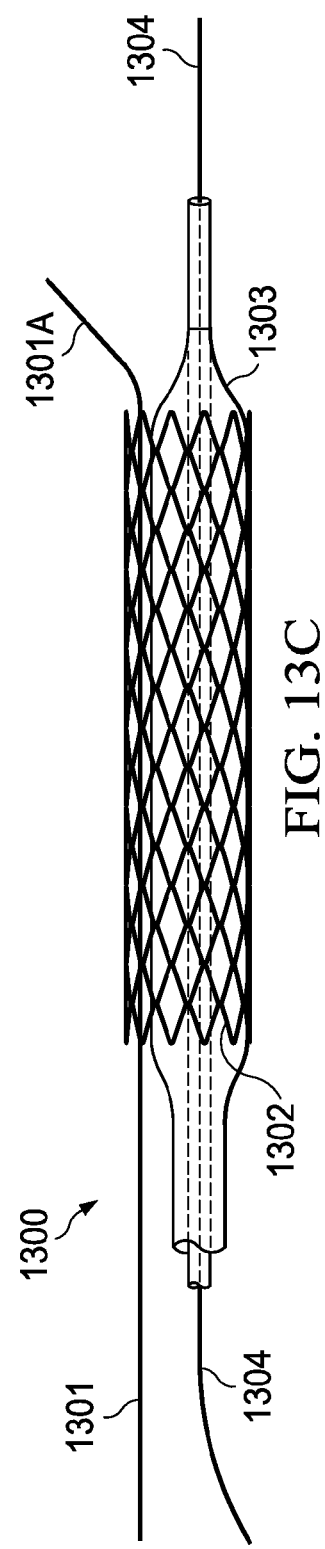
FIG. 13A
FIG. 13B
FIG. 13C

DEPLOYMENT OF STENTS WITHIN BIFURCATED VESSELS

CROSS-REFERENCE TO RELATED APPLICATIONS

This specification claims the benefit of the filing date of U.S. Provisional Patent Application No. 61/528,968, which is titled "Systems and Methods for Deploying Stents within Bifurcated Blood Vessels" and was filed on Aug. 30, 2011, the disclosure of which is hereby incorporated by reference herein in its entirety.

TECHNICAL FIELD

This specification relates generally to systems and methods for stent deployment, and, more particularly, to systems and methods for deploying stents within bifurcated vessels.

BACKGROUND

Bifurcation occurs when a vessel (or main branch) splits into two separate blood vessels (or side branches). Typically, the two side branches are smaller than the main branch. In the case of blood vessels, plaque buildup in the bifurcated region may cause stenosis or otherwise compromise blood flow. These types of lesions may occur within the main branch as well as in the side branches.

Over the years, a few techniques have been developed to attempt to treat lesions at bifurcations. An example of a bifurcation stent delivery device is described in U.S. Patent Application Publication No. 2005/0209673 (Shaked). Specifically, Shaked's device uses an additional lumen to accommodate a secondary guide wire that is inserted into a side branch at a bifurcation. The inventor hereof has recognized, however, that the exit point for the secondary guide wire occurs at the midpoint of the device. As a result, the struts from the exit point may get incorrectly aligned, which may hinder the deployment of a side branch stent.

Another bifurcation device is disclosed in U.S. Pat. No. 7,686,845 (Sequin). Sequin's device uses a self-expanding stent, which the inventor hereof has also recognized tends to be difficult to maneuver and deploy, especially if the plaque burden in the vessel is high. Moreover, the struts of Sequin's stent are subject to grabbing on to plaque during deployment, which may result in inaccurate placement of the stent, damage to the vessel, plaque shift, dissection, or even plaque embolization.

SUMMARY

The currently existing limiting factors for bifurcation stenting can be overcome by novel techniques described herein, which: a) accurately identify the location of the carina in two dimensional angiographic views, b) accurately position the stents at the carina, c) accurately deploy the stents in relation to the carina, d) position wires in the main lumen and the side branches without going through stent struts, e) cover the entire area of the bifurcation so as to get a smooth luminal outcome initially without plaque protruding within the lumen (e.g., 100% coverage of the area is particularly important to obtain the anti-restenosis benefit of drug eluting stents), f) avoid stent struts from protruding within the lumen where blood flows—a problem associated with stent thrombosis, g) allow for reintervention in the future to treat new lesions distally or restenosis of the bifurcation without being hindered by the previously deployed bifurcation stents (e.g., the absence of jailed side branches provides natural anatomic side branch access later), h) allows for completion of a bifurcation stenting procedure with predictable, timely success without complications in the hands of competent operators with common and adequate skills, i) result in low radiation and limited contrast use, j) avoid the need for bypass surgery as the first option or as a complication of the procedure, k) use available (albeit off-label) stent technology to achieve successful results, and 1) creates the possibility that industry can adapt these changes without the need to invent new stents, but instead by modification of existing balloons and channels.

Systems and methods for accurately deploying stents within bifurcated vessels are disclosed. In an illustrative, non-limiting embodiment, a method may include inserting a device into a bifurcated vessel (i.e., a coronary or non-coronary blood vessel, a tracheobronchial tree, a venous system, a ureter, etc.), the device including a balloon catheter and a stent, the stent surrounding at least a portion of the balloon catheter, the balloon catheter including a first lumen configured to accept a first guide wire, the first guide wire exiting the device at a distal end of the balloon catheter, and the bifurcated vessel including a main branch, a first side branch, a second side branch, and a carina region between the first and second side branches.

The method may also include advancing the device within the main branch of the bifurcated vessel over the previously placed first guide wire until the device reaches the carina region. The first guide wire may be maneuvered into the first side branch and/or a second guide wire may enter the second side branch. Also, the second guide wire may exit the device immediately beyond the distal edge of the stent that surrounds the balloon catheter from under the stent. The distal edge of the stent may be placed at or just ahead of the distal tapered edge of the balloon (e.g., the proximal edge of a distally located tapered portion of the balloon). As the stent approaches the carina of the bifurcation, the second wire may enter the second side branch, thereby physically positioning the distal edge of the stent at the carina.

The method may further include deploying the stent within the main branch of the bifurcated vessel by inflating the balloon when the stent is so positioned. In some cases, the diameter of the stent and balloon may be sized for the main branch. The tapered portion of the balloon may be in the first side branch such that it does not push the stent back if the stent is located sufficiently at or slightly ahead of the tapered shoulder. As the balloon is being deflated, the second wire that is under the stent exterior to the balloon may be advanced forward into the second side branch. In this manner, each side branch receives a wire, and both these wires are located within the lumen of the stent of the main vessel. Subsequently, kissing balloons may be used to expand and/or splay this stent to conform to the wider lumen at the bifurcation.

In some implementations, a bifurcation stent balloon device for accurate deployment at the bifurcation may have been pre-assembled in vitro. Further, such a device may include any available drug coated stent as well as non-drug coated, bare-metal stents (although it is recognized that the latter may result in a higher likelihood of stenosis). The method may also include reconfiguring the device prior to inserting the device into the bifurcated vessel. This may include, for example, sliding the stent off of the balloon catheter. The method may also include placing the second guide wire between an inner surface of the stent and an outer surface of the balloon catheter, and sliding the stent back onto the balloon catheter with the distal edge of the stent positioned at the distal, tapered edge of the balloon catheter (e.g., as identified by a distal balloon marker, or the like). In some cases, the stent may be crimped onto the balloon at its new distal forward location. The crimping of the stent may be achieved, for example, by firmly winding a #2 silk suture over the stent.

In other implementations, a novel balloon catheter may include a second lumen, the second lumen configured to accept the second guide wire, a portion of the first guide wire exiting the device at the distal end of the balloon catheter in parallel with respect to a portion of the second guide wire exiting the device at the tapered edge of the balloon catheter. For example, an edge of the stent may be positioned at the tapered edge of the balloon catheter. As such, the first guide wire may be configured to exit the first lumen at a center of the distal portion of the balloon catheter, and the second guide wire may be configured to exit the second lumen at a periphery of the balloon on the balloon catheter.

As such, the second wire may be maneuvered and/or advanced into the second side branch as the stent approaches the bifurcation. It is noted that the crossing profile of such a configuration may be suitable for numerous applications. The second wire lumen may be placed under the stent and extend backwards to the hub of the balloon attached to the shaft or free from the shaft up to the stent. Alternatively, the second lumen may be located only at the balloon under the stent. In the latter case, the second wire may be pre-positioned into the second side branch with due care taken that the two wires remain parallel and do not wind around the each other. If necessary, this parallel position of the wires may be accomplished, for instance, using a dual lumen introducer device or the like.

In various situations, deploying the stent within the main branch of the bifurcated vessel may include inflating the balloon catheter to deploy the stent while maintaining access to the first side branch of the bifurcated vessel via the first guide wire and/or to the second side branch of the bifurcation via the second guide wire. Moreover, deploying the stent within the main branch of the bifurcated vessel may include applying a first kissing balloon technique to expand and/or splay the distal end of the stent. The method may then include deploying another stent within the first side branch of the bifurcated vessel using the first guide wire and/or deploying another stent within the second side branch of the bifurcated vessel using the second guide wire.

In some cases, the stent may be sized appropriately for each side branch vessel. A kissing stent technique may be used with accurate placement of the stents using the visualized splayed first stent in the main branch and the visualized proximal edge of the stents in each side branch, so as to accurately deliver the stents at the carina. To avoid damage to the vessels, high-pressure inflation of one stent (e.g., ~12 atm) may be accompanied with a lowering of the pressures in the other balloon (e.g., ~3 atm). Thereafter, both balloons may be brought to the same medium pressures (e.g., ~6 atm), and then both may be deflated at the same time so as to leave the carina in a central position. The two balloons may be pulled back into the main branch stent and inflated in a similar fashion to ensure that the splayed proximal stent and the two branch stents are pushed into the wall of the vessel, thus leaving behind a smooth true pantaloons bifurcation configuration.

In another illustrative, non-limiting embodiment, a method may include receiving a premanufactured assembled device including a balloon catheter and a stent, the stent surrounding at least a portion of the balloon catheter, the balloon catheter including a first lumen, the first lumen configured to accept a first guide wire. The method may also include placing the stent on the balloon catheter after adding a second guide wire between an inner surface of the stent and an outer surface of the balloon catheter. The method may further include crimping the stent back onto the balloon catheter.

The method may also include advancing the balloon catheter within a vessel using the first guide wire until the balloon catheter stops at a carina of a bifurcation due, at least in part, to the carina contacting the second guide wire, and deploying the stent between a first side branch and a second side branch of the bifurcation. Then, the method may include delivering a second stent to the first side branch of the bifurcation using the first guide wire and/or delivering a third stent to the second branch of the bifurcation using the second guide wire.

In yet another illustrative, non-limiting embodiment, a device may include a balloon catheter including a first lumen and a second lumen, the first lumen configured to receive a first guide wire and the second lumen configured to receive a second guide wire, the first lumen having a first exit at a center of a distal end of the balloon catheter, and the second lumen having a second exit at a shoulder of the balloon catheter. The balloon catheter, upon being inflated, may have a conical portion between the shoulder and the distal end.

BRIEF DESCRIPTION OF THE DRAWINGS

Reference will now be made to the accompanying drawings, wherein:

FIGS. 2A-E are diagrams of dual-lumen balloon catheters according to some embodiments.

FIGS. 4A-H are diagrams of bifurcation stent delivery devices according to some embodiments.

FIG. 12B demonstrating the final results of the creation of a true pantaloons bifurcation stenting configuration.

FIGS. 13A and 13B are simplified diagrams of an open-cell and a closed-cell stent according to some embodiments.

FIG. 13C is a diagram of a bifurcation stent delivery device employing a single-lumen catheter, according to some embodiments. Here the second wire is trapped under the stent by crimping the stent over it.

Figure 1:
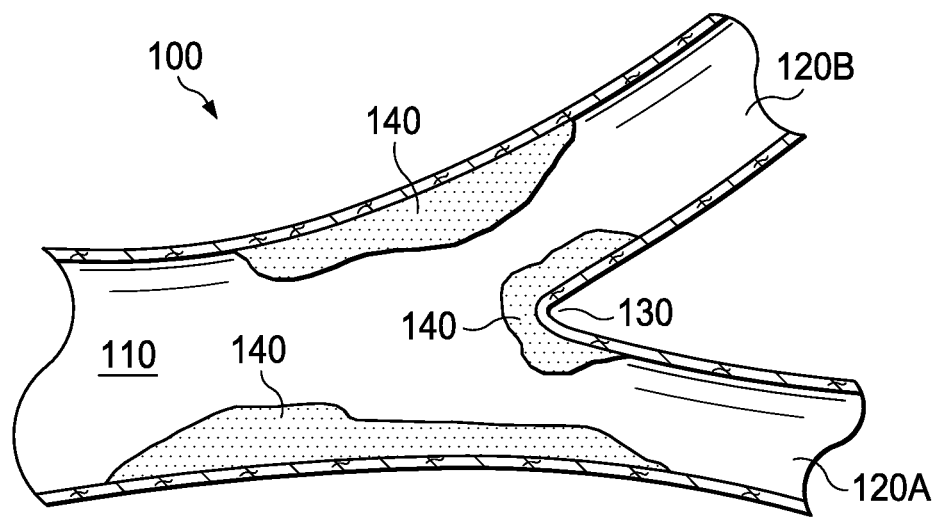
FIG. 1 is a diagram of a bifurcated vessel.

While this specification provides several embodiments and illustrative drawings, a person of ordinary skill in the art will recognize that the present specification is not limited only to the embodiments or drawings described. It should be understood that the drawings and detailed description are not intended to limit the specification to the particular form disclosed, but, on the contrary, the intention is to cover all modifications, equivalents and alternatives falling within the spirit and scope of the claims. Also, any headings used herein are for organizational purposes only and are not intended to limit the scope of the description. As used herein, the word "may" is meant to convey a permissive sense (i.e., meaning "having the potential to"), rather than a mandatory sense (i.e., meaning "must"). Similarly, the words "include," "including," and "includes" mean "including, but not limited to."

DETAILED DESCRIPTION

This specification discloses systems and methods for accurately deploying stents within bifurcated vessels. Examples of "bifurcated vessels" include, but are not limited to, bifurcated blood vessels (coronary, carotid, iliac, or other blood vessels), tracheobronchial trees, venous systems, ureters, etc. Although the embodiments discussed below occasionally refer to specific types of vessels (e.g., blood vessels), it should be understood that these examples of intravascular stents are provided for sake of illustration only, and not by way of limitation. Moreover, it should be noted that the various embodiments illustrated in the figures and discussed below are not necessarily drawn to scale, but are instead presented with dimensions intended facilitate their understanding.

In various embodiments, the methods described herein include deploying a stent at the main branch of a bifurcated vessel by positioning the stent accurately at the carina of the bifurcation while maintaining access to one or more side branches, and then deploying one or more additional stents in the side branches of the bifurcation. In some implementations, these methods may be performed by employing at least two distinct types or groups of stent delivery devices. A first group of devices includes a balloon catheter manufactured with two or more lumens or channels configured to accommodate two or more separate guide wires (i.e., a dual-lumen catheter as shown in FIGS. 2A-D, or a triple-lumen catheter, as shown in FIG. 2E). The pre-manufactured models may include multiple balloons in some embodiments. A second group of devices includes alternatives to the pre-manufactured dual-lumen catheter. An existing single-lumen balloon catheter may be modified so that it is capable of performing the same or similar operations as the pre-manufactured models. For example, a secondary guide wire may be placed between the stent and a single-lumen balloon catheter in an "off-label" procedure (e.g., FIG. 13C). Additionally or alternatively, a dual-balloon configuration with a single stent crimped over two balloons may be designed to help position the stent at the carina (e.g., FIG. 16A). Additionally or alternatively, a stent may be crimped over a combination of a balloon catheter and a long tube catheter with an approximately 0.014-inch wire lumen or the like to facilitate accurate delivery at the carina while maintaining dual side branch access through the stent lumen (e.g., FIGS. 16B and 16C). These various devices, as well as their corresponding manufacturing and delivery methods, are described in turn below.

Stent Delivery with Multi-Lumen Balloon Catheters

In some embodiments, stent delivery devices may employ balloon catheters manufactured with two or more lumens (the first group or type of devices described above). For example, in a dual-lumen configuration, a main lumen may be located in the axial center of the balloon shaft, and may be configured to house a main guide wire. A secondary lumen may be located along the side of the balloon shaft, and may be configured to house a secondary guide wire. The exit point for the secondary lumen may be at the distal end of the balloon, and may occur where the balloon tapers—i.e., at or near a "shoulder region" of the balloon. This secondary guide wire may maintain access to a side branch of a bifurcated vessel during a stent deployment procedure. In some embodiments, three stents may be deployed, one in each branch of the bifurcation. The device may maintain a low profile to ensure that it fits in the entity being treated (e.g., a coronary vessel or other type of vessel). The stent(s) may be chosen, for example, based on the size of the vessel and the length of the lesion.

In various embodiments, the stent may be positioned on the balloon so that the stent is at the shoulder of the balloon, just as the balloon tapers. As the inventor hereof has discovered, when the balloon is inflated for stent expansion, the portion of the balloon distal to the stent should immediately taper and the balloon should not push the stent back from its desired location within the vessel directly at the carina. In contrast, conventional stent delivery systems typically place the stent in the center or middle of the balloon, with a ~0.5 to 1 mm of balloon extending or "overhanging" proximal and distal to the stent. The distal portion of the balloon beyond the distal edge of the stent is generally larger than either side branch. During stent inflation, the ends of the balloon that are not covered by the stent expand first. Since side branches are generally smaller than the main branch, when there is a size mismatch of the distal balloon with respect to the size of the side branch vessel, the distal balloon-end expansion in a conventional delivery system invariably displaces the stent away from the carina. Again, at least in part because certain of the techniques described herein allow accurate positioning of the stent at the carina of the bifurcation, these techniques represent a significant improvement over conventional delivery systems. Conventionally, because of branch vessel overlap, it is difficult to identify the true bifurcation. The bifurcation seen by angiography may not accurately correspond to the true anatomical bifurcation. This difficulty is overcome by the technique described herein, because the anatomical bifurcation is physically identified. This not only guarantees that the stent is placed accurately at the bifurcation, it also saves the patient from being exposed to additional contrast and radiation.

A 0.014-inch guide wire or the like may be placed in each lumen or channel of the balloon. The assembled device may be placed in the vessel using the main guide wire. As the device moves along main guide wire through the vessel, the secondary guide wire may be guided into a side branch. The device may be advanced, for example, until it naturally stops at the carina of the bifurcation due to the secondary wire positioned into the side branch. At this point, the operator may know or sense that the device is positioned accurately at the carina. For example, the secondary wire in the second side branch may be observed to buckle slightly and a resistance to forward progress of the stent will be felt physically by the operator. Additionally or alternatively, radiolucent markers or the like on the balloon shaft, stent, and/or distal tip of the tube or channel under the stent may facilitate positioning of the balloon during this procedure. Also, in some cases, the uninflated stent may have a distal marker or may be more visible because it is not inflated and/or because it is more radiolucent, as is the case of platinum chromium stents (e.g., ION® or PROMUS® stents).

The balloon catheter may then be inflated and the stent deployed. In this manner, access to the side branch and main branch within the lumen of the stent may be maintained with the two guide wires. Next, a first kissing balloon technique may be used to splay the stent to conform to the bifurcation. The two balloons may be sized as per the approximate diameters of each side branch so as to splay the stent appropriately without damaging the side branches. Once the kissing balloons have been inflated, the stent in the main branch may be splayed across the carina. Thereafter, stents of the appropriate size may be deployed in a kissing manner into the side branches of the bifurcations. These two stents may be positioned so that the proximal part of the respective stents is exactly at the carina. A second kissing balloon technique may be used to further inflate the branch stents and the main vessel stent, and further cause opposition of the stents into the intima of the vessel. High-pressure inflations may be used.

For sake of illustration, a typical procedure for kissing stents deployment may be conducted as follows. When one of the kissing balloons is inflated to approximately ~10-16 atm, the other balloon may be inflated to approximately ~4 atm (and vice versa for the other stent). Thereafter, both balloons may be brought down to approximately ~5-8 atm and deflated at the same time to ensure that the carina is correctly positioned. It should be understood, however, that the inflation pressures to be used are dependent on the size of the vessel, the compliance of the inflating balloons, manufacturer recommendations, etc. In the dual balloon stent configuration, for example, the two balloon sizes selected may be small enough to not damage the main vessel and yet capable of pre-dilating the distal side branches to facilitate the kissing stents to follow.

In various applications, a stent delivery device may be used to deploy stents designed to treat stenosis and/or other vessel conditions. Techniques for deploying these stents accurately at bifurcated lesions are described below.

Turning now to FIG. 1, a diagram of a bifurcated vessel is depicted. Generally, the lengths and diameters of the various elements of bifurcated vessel 100 may vary depending upon their location in a patient's body. As illustrated, bifurcated vessel 100 includes main branch 110, which splits between side branches 120A-B. Carina 130 represents a region of bifurcated vessel 100 where side branches 120A-B are joined together. In some cases, carina 130 may also be referred to as a "vertex" or "crotch point" of bifurcated vessel 100. Plaque 140 is illustrated along the surfaces or walls of bifurcated vessel 100 to represent stenosis or other types of lesions.

FIG. 2A is a diagram of a dual-lumen balloon catheter according to some embodiments. In particular, balloon catheter 200A may include proximal tapered end 210 and distal tapered end 220. Catheter 200A may also include main or primary guide wire lumen (or channel) 230 as well as side or secondary guide wire lumen (or channel) 240. Main guide wire lumen 230 may include exit 250, and may be configured to receive a first guide wire (i.e., a main or primary guide wire—not shown) through main wire port 201. Conversely, side guide wire lumen 240 may include end 260, and may be configured to receive another guide wire (i.e., a side or secondary guide wire—not shown) through second wire port 202. Balloon inflation port 203 may be utilized deliver dilute contrast or another suitable fluid to lumen 280 or chamber 281 so as to inflate catheter 200A during a delivery procedure. In some cases, lumen 280 or chamber 281 may at least partially surround main guide wire lumen 230.

As illustrated in FIG. 2A, exit 250 of main lumen 230 through shaft portion 251 may be located at or near the center portion (i.e., the axis) of catheter 200A, whereas end 260 of side lumen 240 may be located at or near (e.g., immediately after) proximal edge 270 of distal shoulder region 220 of catheter 200A. It may also be noted that catheter 200A tapers between proximal edge 270 of distal shoulder region 220 (or end 260) and distal edge 271 of distal shoulder region 220, which is where the balloon joins shaft 251 in an approximately conical tapered fashion. Accordingly, proximal edge 270 of distal shoulder region 220 may sometimes be referred to as a "tapered edge," "tapered shoulder," or "shoulder" of catheter 200A.

In some embodiments, proximal edge 270 may be defined as the point along catheter 200A where it begins to taper into region 220. And in some cases, end 260 may be located exactly at proximal edge 270. In other cases, end 260 may be located at a distance from proximal edge 270 so that lumen 240 ends before edge 270 or extends beyond edge 270.

Figure 4C:
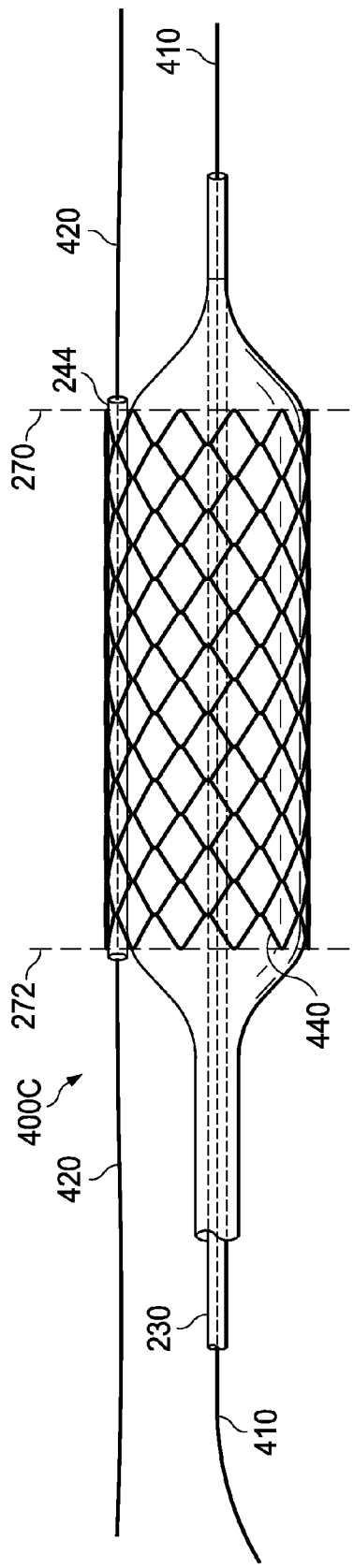

The individual guide wires may be placed through the main vessel and into the two side branches of the bifurcation before the dual lumen stent balloon is loaded. In this case, the guide wires should not be twisted around each other, which would obstruct the movement of the stent balloon as it travels along the guide wires and through the main vessel to the carina location. In some cases, the dual lumen catheter in the configuration of FIGS. 2A-2E may aid in such parallel placement of wires. In the configuration of FIG. 4C, for example, such parallel placement of the guide wires may be achieved beforehand (e.g., the Twin Pass Dual access Catheter model 5200 by Vascular Solutions Inc.).

Figure 4D:
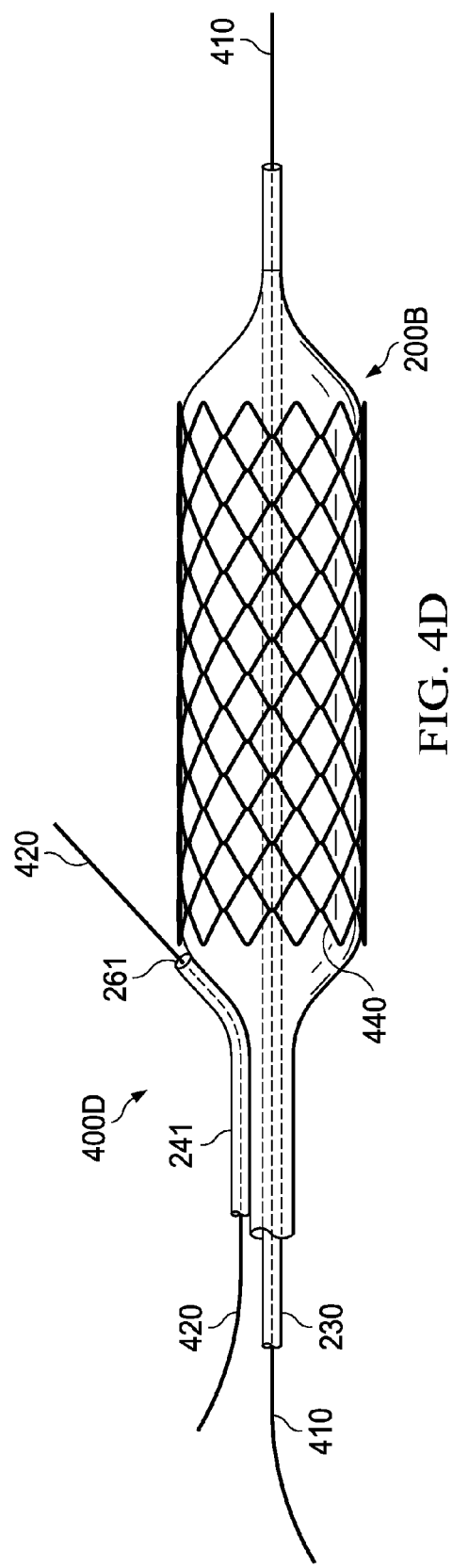
Figure 4E:
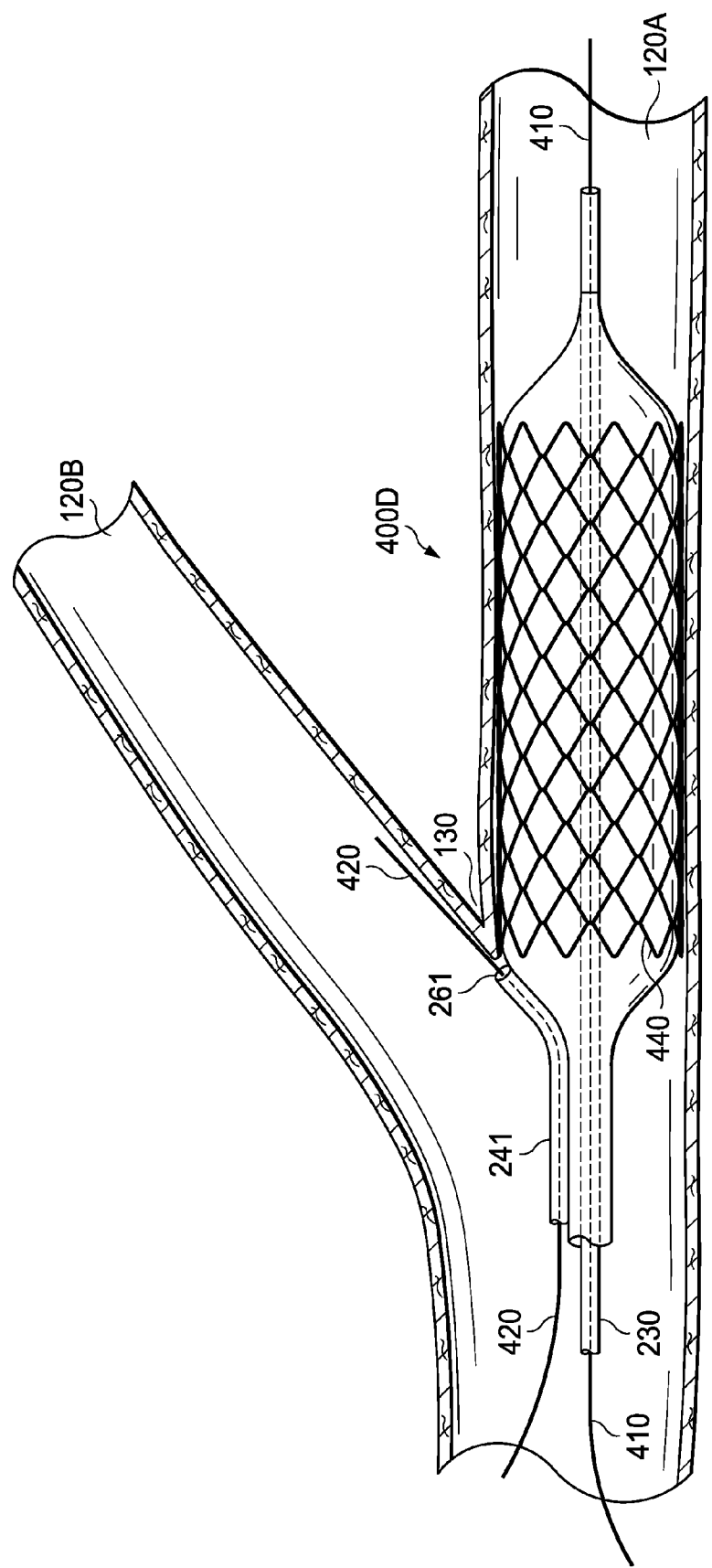

FIGS. 2B-E illustrates alternative embodiments of a dual-lumen balloon catheter. Particularly, FIG. 2B shows side guide wire lumen 241 with end 261 located at distal edge 272 of proximal tapered portion 210 of catheter 200B. In some cases, the embodiment of FIG. 2B may be used, for example to deliver a stent distal to the carina of a bifurcated vessel (as shown in FIGS. 4D and 4E).

FIG. 2C shows side guide wire lumen 242 with first exit 262 located at or near distal edge 272 of proximal tapered portion 210 (i.e., a "first tapered edge") and end 260 located at or near proximal edge 270 of distal tapered portion 220 (i.e., a "second tapered edge") of catheter 200C. As such, the embodiment of FIG. 2C is a "universal" balloon catheter with the capability to accurately deliver a stent located proximal or distal to the carina.

FIG. 2D shows an alternative configuration of side guide wire lumen 243 with end 263 located at proximal edge 270 of distal tapered portion 220, but running alongside main guide wire lumen 230 for a least a portion of the length of balloon catheter 200D.

FIG. 2E shows yet another alternative configuration of a universal balloon catheter 200E with two wire lumens; lumen 240 terminating at opening 260 at edge 270 and lumen 244 terminating at opening 264 at edge 272.

Figure 3:
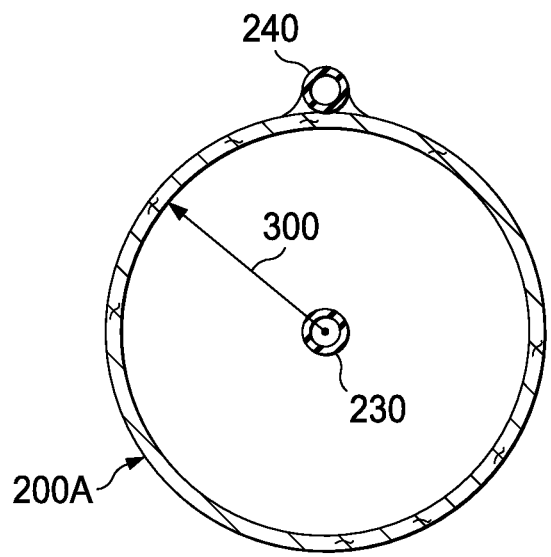
FIG. 3 is a cross-sectional view of the balloon catheter according to some embodiments.

Referring to FIG. 3, a cross-sectional view of balloon catheter 200A of FIG. 2A is depicted. In this embodiment, lumen 230 is usually located approximately at the center of catheter 200A, and lumen 240 is located outside the perimeter of catheter 200A. In alternative embodiments, lumen 240 may also be located along the perimeter but within balloon catheter 200A. Again, end 260 of lumen 240 may be located at or near shoulder region 270 of catheter 200A, near a point where catheter 200 begins to taper off (i.e., proximal edge 270 of distal shoulder region 220).

In various embodiments, radius 300 of catheter 200A may be designed so as to determine an angle or degree of tapering of distal end 220 and to facilitate insertion of catheter 200A in vessels of varying sizes. For example, a small radius 300 may reduce the profile of catheter 200A. Conversely, a large radius 300 may allow bifurcations with large angles and/or diameters to be properly treated using catheter 200A. In a number of applications, the distal balloon end may taper from the shoulder onwards as rapidly as technically feasible. Moreover, in some cases, a set of two or more catheters 200A with different diameters may be available, and a user or operator may select a suitable one among the set based on a location within the patient's body where a stent procedure will be performed (e.g., coronary arteries may require low profile, etc.).

Figure 4H:
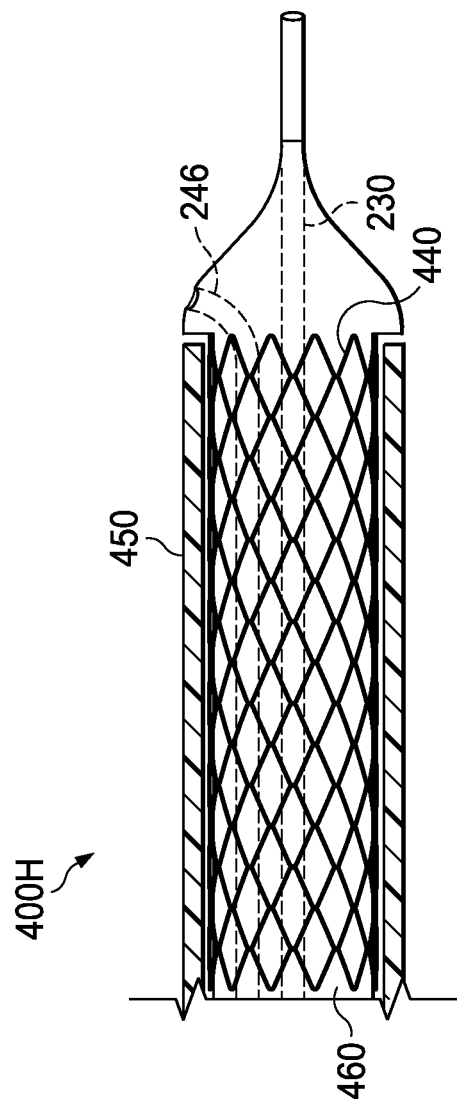

It should be noted that, except in FIGS. 6, 7, 16A-C and 17A (where the stent balloon diagram represents an unexpanded balloon with the stent crimped on it), all other balloon diagrams (FIGS. 2A-E, 3, and 4A-G) are shown with the balloon expanded somewhat, but this is entirely for illustrative purposes. FIG. 4H is a self-expanding stent and does not require a balloon for deployment. Generally speaking, balloon lumen 281 is collapsed when the stent is crimped on the balloon (i.e., the balloon is folded in an unexpanded state under the crimped stent). FIGS. 4E, 8-11, 12A, and 17B may represent expanded versions of the stent-balloon configuration in some situations.

FIG. 4A is a diagram of bifurcation stent delivery device 400A according to some embodiments. As illustrated, device 400A utilizes the balloon catheter 200A depicted in FIG. 2A. Specifically, stent 440 may be positioned on the outer surface of balloon catheter 200A. In some cases, a distal edge of stent 440 may be aligned with edge 270 of shoulder region 220 on catheter 200A. Main guide wire 410 may be positioned in a vessel in a location desired by the operator or surgeon. Note that in most instances, wire 410 may be placed in the vessel across the lesion in the main branch 110 (shown in FIG. 1) and further across the first side branch 120-A (shown in FIG. 1), which is chosen because it is the more difficult lesion to cross. Wire 420 may be placed across the other side branch 120B (shown in FIG. 1) beforehand or after the stent approaches the carinal bifurcation point 130 (shown in FIG. 1).

Main guide wire 410 is inserted through main lumen 230 of catheter 200A into end 250 and out of proximal end 201 (shown in FIG. 2). Catheter 200A is then advanced along guide wire 410 into the vessel and positioned as desired. Similarly, side guide wire 420 may be inserted through side lumen 240 of catheter 200A into end 260 and out end 202 (also shown in FIG. 2). In other embodiments, as shown in FIGS. 2B and 2C, lumen 240 may terminate at the distal shoulder 272 of tapered region 210, where side guide wire 420 may exit through end 261 or exit 262 (shown in FIGS. 2B and 2C). Alternatively, the side guidewire 420 may be introduced through the proximal end 202 into lumen 240 to exit from the end 260, 261 or 262 as the case may be, after the catheter 200A has already been advanced into the artery close to the carina.

FIG. 4B shows an alternative configuration for bifurcation stent delivery device 400B according to some embodiments. Specifically, device 400B employs balloon catheter 200D shown in FIG. 2D.

FIG. 4C shows stent delivery device 400C where the second side guide wire channel 244 is approximately the same length as the cylindrical portion of the balloon and slightly longer than the stent 440 spanning from shoulder 272 to shoulder 270. In this configuration, both wires 410 and 420 may be placed across the main branch and side branches 120A and 120B (shown in FIG. 1) before threading the guide wires into the stent delivery device 400C. Wires 410 and 420 may be of approximately the same lengths allowing for one catheter to be exchanged for another.

FIG. 4D illustrates a bifurcation stent delivery device 400D using balloon catheter 200B of FIG. 2B. In this embodiment, as previously shown, side guide wire 420 may leave side guide wire lumen 240 through end 261. As such, this device configuration may be particularly well suited for accurately placing stent 440 at the carina beyond the main branch and into one of the side branches 120A or 120B (shown in FIG. 1).

FIG. 4E shows device 400D positioned within side branch 120A beyond carina 130. As device 400D is insertion into side branch 120A, guide wire 420 causes device 400D to stop at carina 130 with stent 440 accurately located at carina 130 and extending into branch 120A. In some cases, such a technique may be used, for example, to preserve side branches and/or to prevent jailing of the side branch—i.e., prevent the stent from deployed in such a way as to block or partially block access to the side branch Besides accurate positioning of the stent beyond the carina, the added advantage of this technique is that the wire 420 maintains access to the side branch 120B in case side branch 120B needs intervention should the carina shift laterally and obstruct blood flow to the side branch 120B.

FIG. 4F shows bifurcation stent delivery device 400F employing balloon catheter 200C of FIG. 2C. Particularly, balloon 200C may have two exit points (260 and 262) in lumen 242 for guide wire 420. For example, wire 420 may leave catheter 200C through exit 260 (at or near edge 270 of distal tapered region 220) for placement of stent 440 at the carina of a bifurcation and just before a side branch. Proximal exit point 262 (at or near edge 272 of proximal tapered region 210) may be used to place stent 440 accurately after the carina and within a side branch.

FIG. 4G shows device 400G with a balloon catheter with three lumens—center lumen 230 and side lumens 240 and 245. Each lumen is configured to hold a different guide wire 410, 420, 430. As such, device 400G may be particularly well suited for a procedure involving a trifurcation or the like (e.g., where a vessel includes a main branch splitting into three side branches). In this case, each of guide wires 410, 420, 430 may facilitate positioning a stent with respect to each of three side branches.

FIG. 4H shows bifurcation delivery device 400H in a configuration suitable for use with self-expanding stents. Particularly, device 400H includes outer sheath 450, self-expanding stent 440, and inner shaft 460, as well as main lumen 230 and side channel 246. Delivery of stent 440 may be accomplished by unsheathing stent 440, for example, by pulling back outer sheath 450. In the experience of the inventor hereof, the self-expanding stent should be oversized to the extent that it has to splay and closely conform to the spread of the bifurcation. Often the stent has to be partially released a millimeter or two before the carina and simultaneously gently advanced forward to get it to the carina and sometimes a fraction of the strut length beyond the carina. Thus, a method of deploying a self-expanding stent may be different from another method using a balloon expandable stent. Typically, self-expanding stents are intended for peripheral use. A bifurcation deployment may be considered, for example, the common Iliac bifurcation to the external and internal Iliac or the common femoral to superficial femoral and profound femoris bifurcation. The use of a second wire lumen 246, as described herein, may allow accurate placement of the stent at the bifurcation while allowing for luminal placement of both of the wires in each side branch vis-à-vis the stent in the main vessel.

Figure 5:
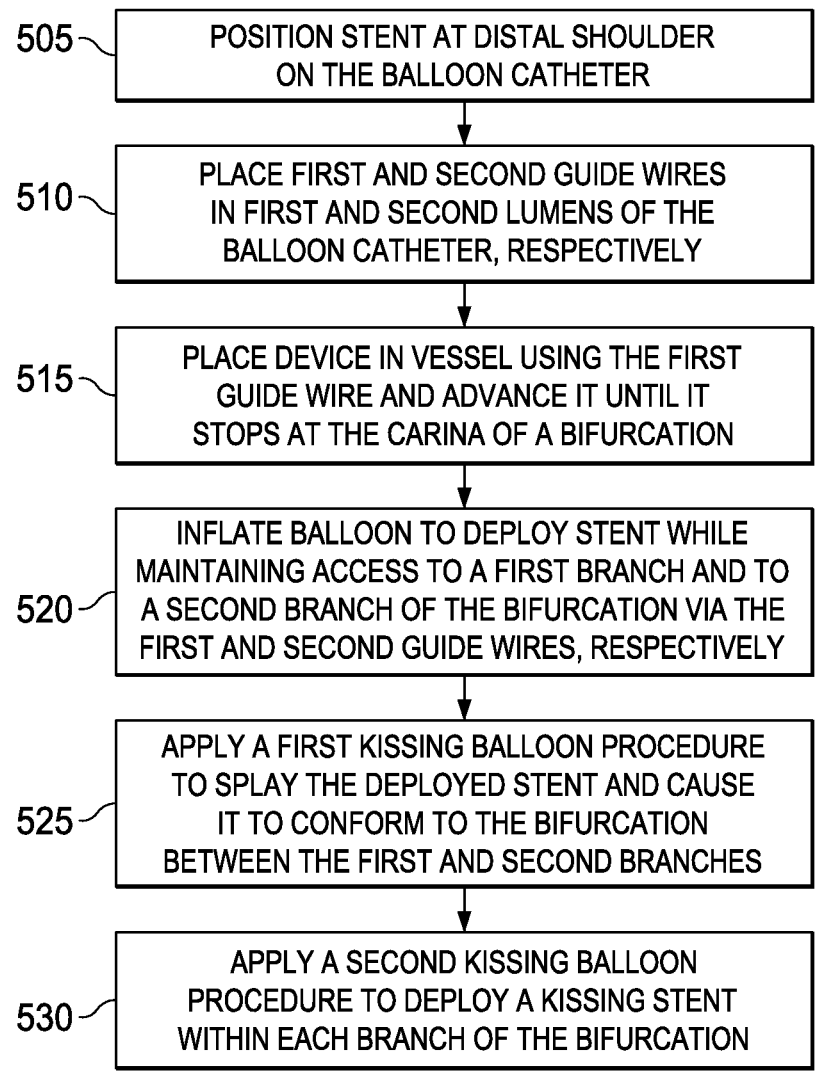
FIG. 5 is a flowchart of a bifurcation stent delivery technique according to some embodiments.

FIG. 5 is a flowchart of a bifurcation stent delivery technique according to some embodiments. To further illustrate this technique, reference is also made to FIGS. 4A-G and 6-12. At block 505, a user or operator may position a stent (e.g., stent 440 in FIG. 4A) with its edge at or near at or near a proximal edge (e.g., 270) of distal shoulder region (e.g., 220) of a balloon catheter (e.g., 200A). At block 510, the user may insert a first guide wire (e.g., main wire 410) in a first lumen, channel, or cavity (e.g., main lumen 230) of the catheter and/or may also insert a second guide wire (e.g., side wire 420) in a second lumen, channel, or cavity (e.g., side lumen 240) of the catheter. In other cases, however, a medical device manufacturer or the like may perform the operations indicated in blocks 505 and 510 to provide a pre-assembled bifurcation stent delivery device as shown in FIGS. 4A-G.

Figure 6:
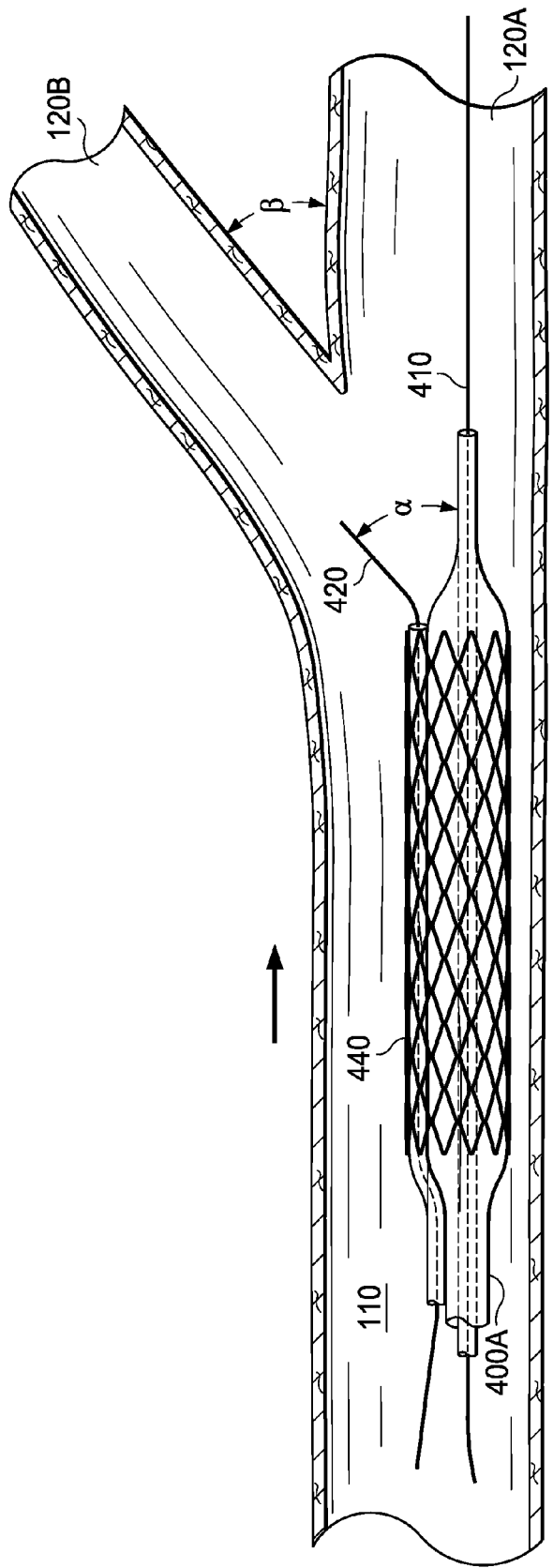
FIG. 6 is a diagram of a bifurcation stent delivery device introduced into a main branch toward a bifurcation lesion according to some embodiments.

At block 515, the user may place the bifurcation stent delivery device in a patient's vessel using the first guide wire. For example, if the main guide wire is the "first guide wire," it may be placed across the mail vessel and into one of the branches. Typically, the first guide wire may be placed across the lesion in the main branch and the side branch that presents the more challenging stenosis to cross. This operation is shown in FIG. 6, as device 400A is introduced into main branch 110 toward the bifurcation into branches 120A and 120B. The second guide wire may be placed in the second branch (e.g. 120B) beforehand or as the stent approaches the bifurcation depending upon the configuration of the bifurcation stent delivery device. In some cases, a portion of side wire 420 leaving the device may be shaped at a first acute angle alpha (α) designed to (at least approximately) match a second acute angle beta (β) between side branches 120A and 120B, and therefore be inserted into side branch 120B. FIG. 6 also shows main wire 410 positioned inside one of the branches (e.g., branch 120A) of bifurcation 100 (for ease of illustration, stenotic plaques are not drawn). It will be understood that the main branch 110 and side branches 120A and 120B as drawn in the figures are merely examples for the purpose of illustration. The stents and methods described herein may be used with any sizes and any configuration of the main branch 110 and side branches 120A and 120B.

Figure 7:
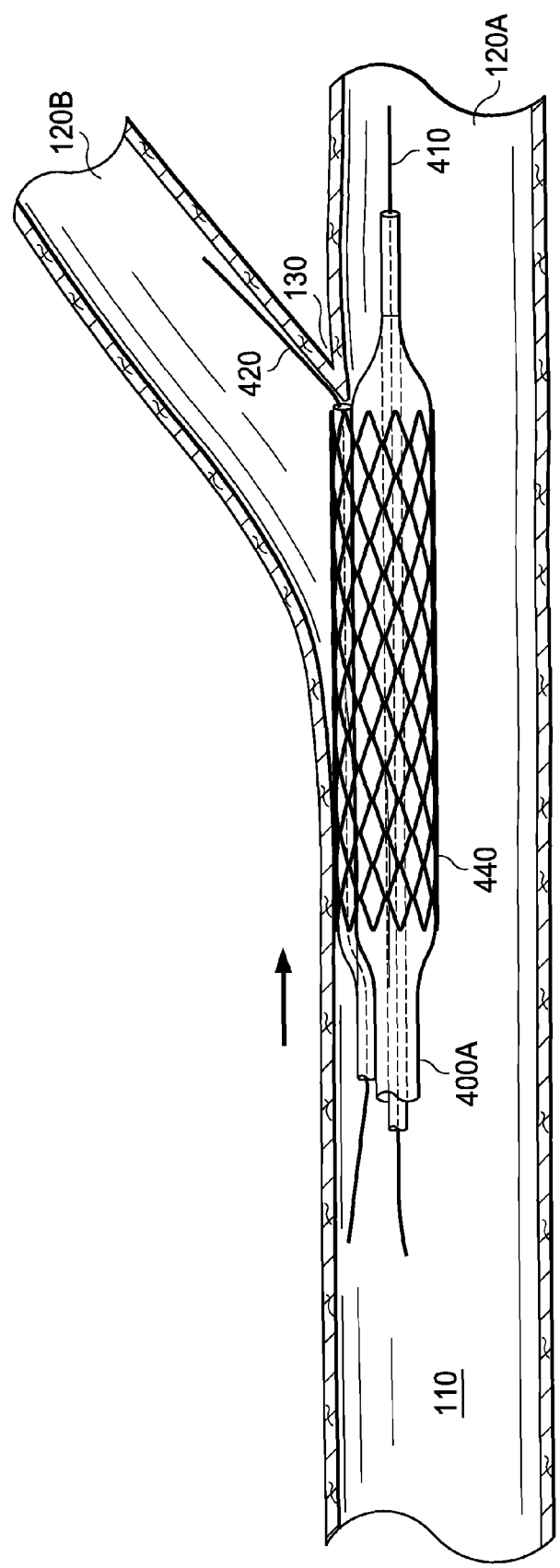
FIG. 7 is a diagram of the bifurcation stent delivery device positioning a stent at the carina of the bifurcation according to some embodiments.

Returning to block 515, the user may advance device 400A until it stops at the carina of the bifurcation. This is illustrated in FIG. 7, where device 400A positions stent (e.g., 440) exactly at carina 130. In particular, FIG. 7 shows that side wire 420 may enter the other side vessels (e.g., 120B), and thus cause the insertion of device 400A to naturally stop at carina 130.

Figure 8:
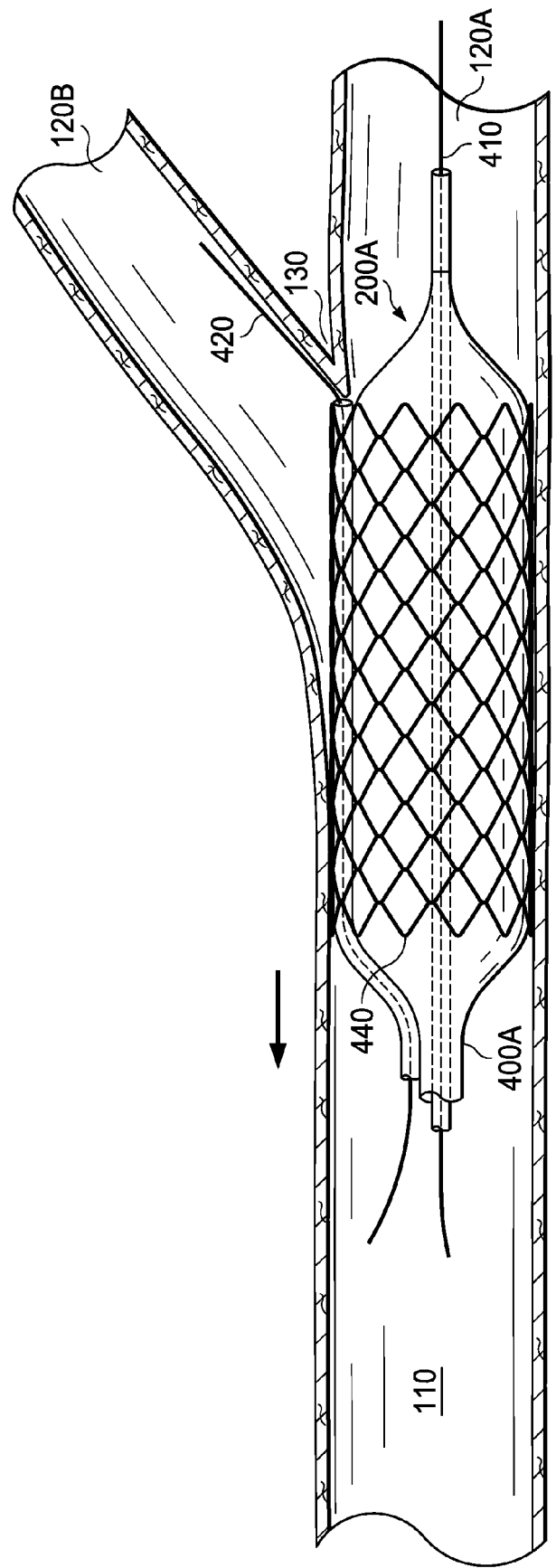
FIG. 8 is a diagram of the bifurcation stent delivery device deploying the stent at the carina according to some embodiments.
Figure 9:
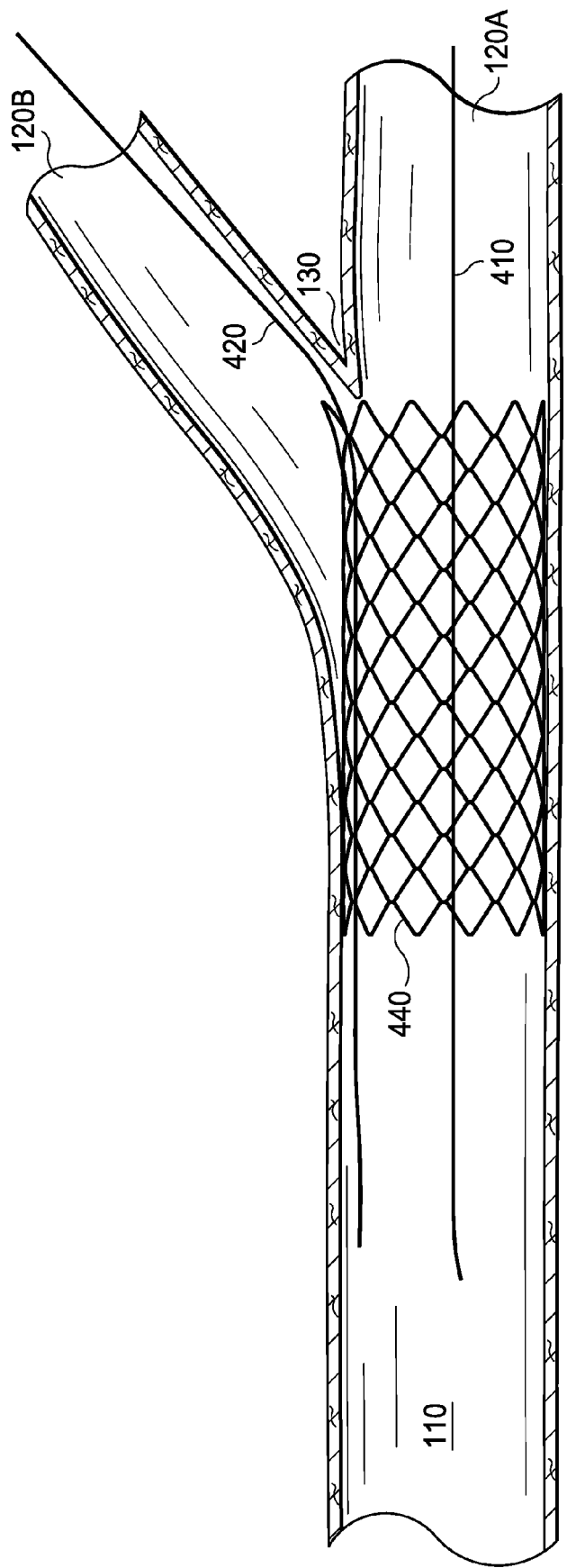
FIG. 9 is a diagram of the stent with the balloon removed and the expanded stent accurately positioned across the carina according to some embodiments.

At block 520, the user may inflate the balloon catheter to deploy the stent while maintaining access to the first and second branches of the bifurcation via the first and second guide wires, respectively. FIG. 8 shows catheter 200A after it has been inflated so that expanded stent 440 is correctly positioned with respect to the bifurcation. FIG. 9 shows stent 440 expanded at carina 130 and straddling it after the catheter 200A has been deflated and removed. FIG. 9 also shows that side guide wire 420 has been positioned deeper within side branch 120B after deflation of catheter 200A. This may be achieved by advancing wire 420 into the side branch 120B simultaneously as the balloon deflates. Subsequently, the balloon catheter may be removed in a manner so that both guide wires (410 and 420) remain in place in each respective side branch. Importantly, it should be noted that both wires (410 and 420) are within the lumen of the stent.

Figure 10:
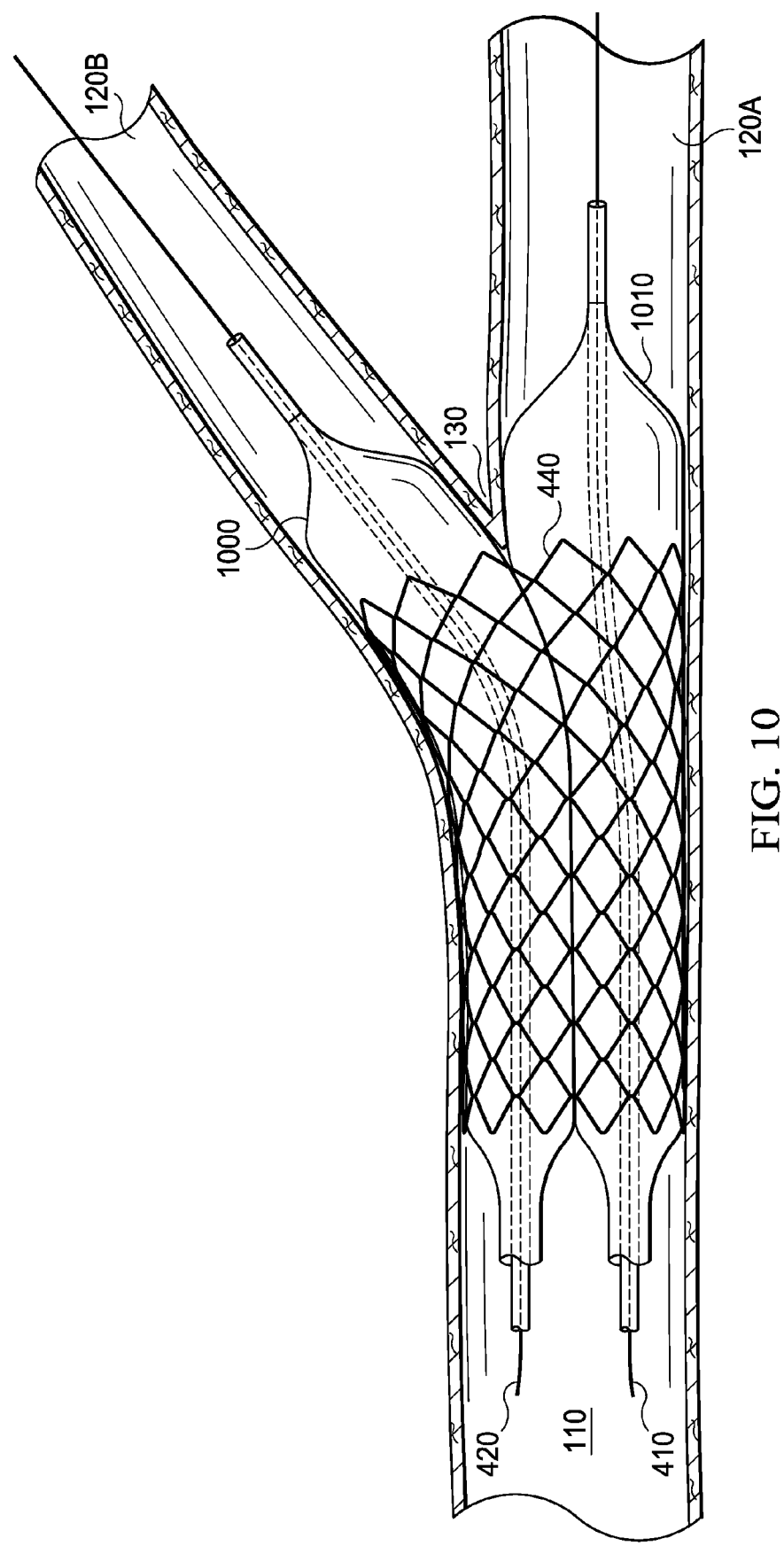
FIG. 10 is a diagram of kissing balloons used to splay the stent across the carina according to some embodiments.
Figure 11:
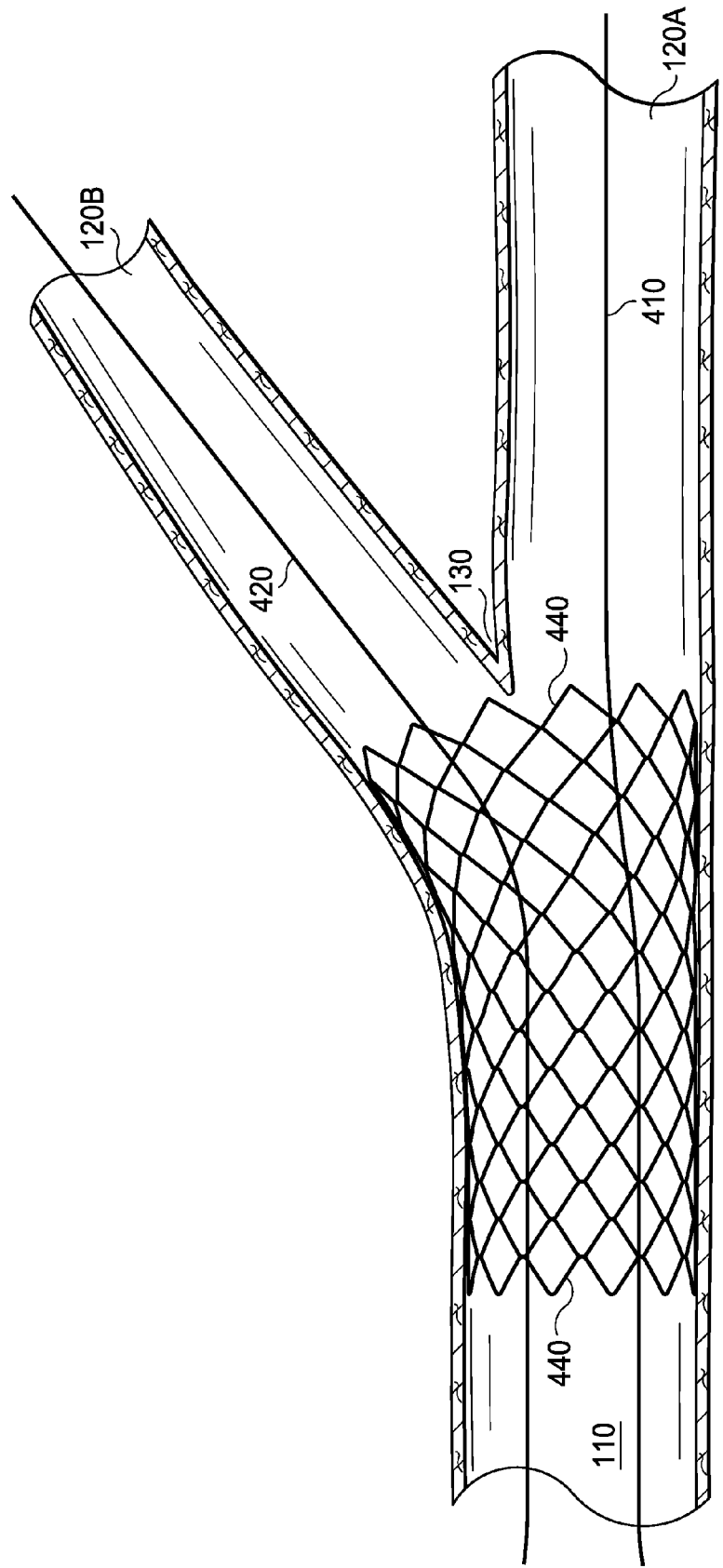
FIG. 11 is a diagram of the stent fully splayed across the carina according to some embodiments.

At block 525, the user may apply a first kissing balloon procedure to splay the deployed stent 440 and to cause it to more fully conform to the walls of the bifurcation between the first and second side branches. FIG. 10 shows balloons 1000 and 1010, which have been advanced along their respective guide wires 420 and 410 through expanded stent 440 and into the side branches. The balloons 1000 and 1010 are inflated, thereby causing stent 440 to further expand and conform to the shape of the vessel at the bifurcation. After inflation of balloons 1000 and 1010, stent 440 is splayed across the bifurcation at carina 130. FIG. 11 is a diagram illustrating stent 440 fully splayed across carina 130 as a result of the first kissing balloon procedure after the balloons have been deflated and removed.

Figure 12A:
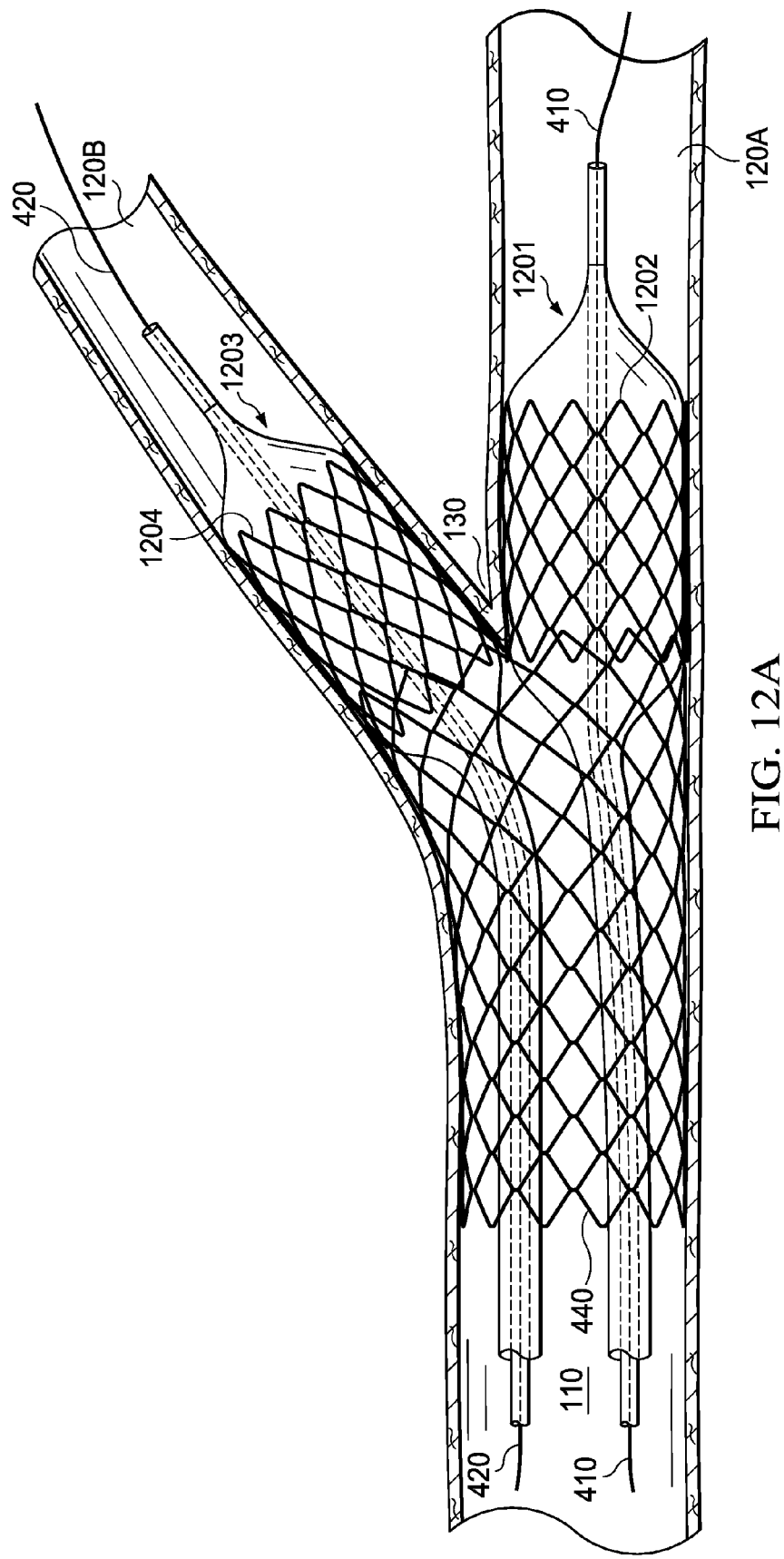
FIGS. 12A and 12B are diagrams of three stents being positioned at the bifurcation according to some embodiments.
Figure 12B:
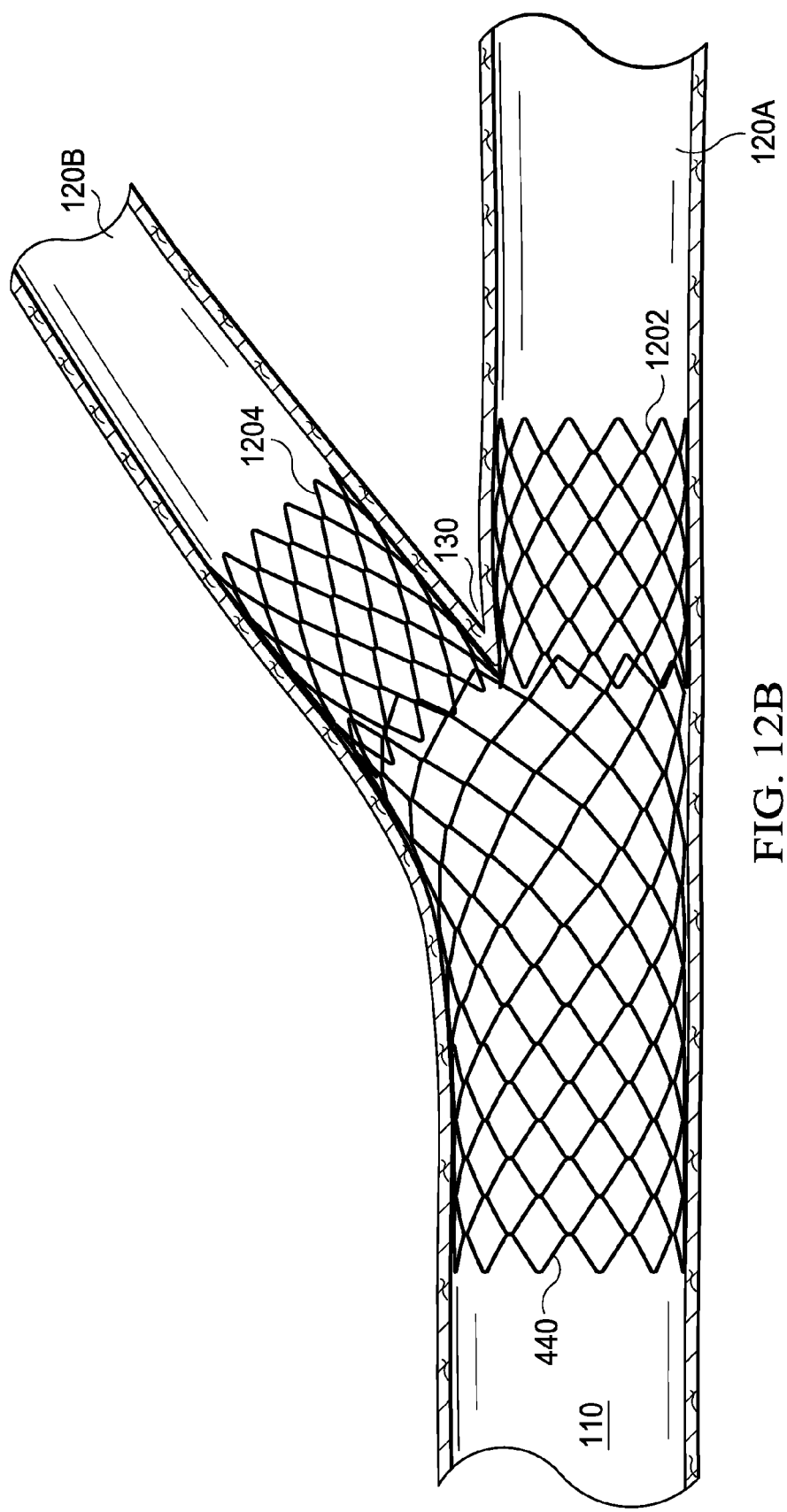

Returning to FIG. 5, at block 530 the user may apply a second kissing balloon procedure to deploy a kissing stent within each branch of the bifurcation. The second kissing balloon procedure is illustrated in FIGS. 12A and 12B. FIG. 12A shows balloon 1201 with stent 1202 and balloon 1203 with stent 1204. Balloons 1201 and 1203 have been advanced along the guide wires 410 and 420, respectively, through expanded stent 440 and into the side branches. Balloon 1201 and first kissing stent 1202 are positioned within first branch 120A and then balloon 1201 is inflated to expand stent 1202. Balloon 1203 and second kissing stent 1204 are positioned within second branch 120B and then balloon 1203 is inflated to expand stent 1204.

FIG. 12B depicts the result of the second kissing balloon procedure with the deploying devices 1201 and 1203 removed from the vessel. As shown in FIGS. 12A and 12B, there may be an area of overlap between or among stents 440, 1202, and 1204 during inflation and after the balloons have been withdrawn. Unlike conventional or traditional bifurcation stenting methods, the methods described herein may ensure that the deployed stents are positioned accurately at the carina and cover the entire bifurcation uniformly. Depending upon the type of stent used, this may allow anti-restenosis drugs to be uniformly delivered to the bifurcation. Additionally, it is also to be noted that the methods described herein may ensure that all stent struts are opposed to the walls of the bifurcation, thus minimizing or otherwise reducing the chance of stent thrombosis.

Therefore, using the techniques outlined above, stents 1202 and 1204 may be positioned at the carina 130. These stents may be the regular pre-mounted stents, and in most cases may not need to be reconfigured in any way. The stents used in the second kissing procedure may be deployed at the same time or sequentially. The configuration shown in FIG. 4E may be used to deploy stents 1202 and 1204 accurately at the carina 130 and beyond. For example, a first stent delivery device may enter the vessel with lumen 230 on the wire 410 and with side branch wire 420 going through lumen 241. This would be used to deploy stent 1202. A second stent delivery device may then enter the vessel with lumen 230 on wire 420 and with side branch wire 410 going through lumen 241. This would be used to deploy stent 1204.

After stents 1202 and 1204 have been deployed, another kissing balloon inflation across the bifurcation (e.g. FIG. 10) may be employed to complete the procedure and cause optimal or otherwise improved expansion and opposition of the stents to the wall of the vessel. This particular stent deployment technique at the carina may save on the amount of radiation and/or contrast usage, and it may improve patients' outcomes due to its ability to position stents accurately at the carina.

Alternatives to Multi-Lumen Balloon Catheters

In some situations, a pre-configured or pre-manufactured dual-lumen balloon catheter may not be readily available to a user. However, one or more of the stent deployment methods described herein may be used with single-lumen, conventional catheters. This is the second group or type of devices referred to above. For example, a dual-guide wire stent may be constructed from a single-lumen catheter stent by adding a second guide wire between the stent and the balloon. The stent may be removed from the balloon and the second guide-wire positioned inside the stent. The stent may then be reinstalled on the balloon.

Starting with a single-lumen catheter, a stent delivery device may be assembled in different ways depending upon the type of stent being used (i.e., a closed-cell stent versus an open-cell stent). For example, the operation of removing the stent from its balloon catheter may be performed differently open-cell versus closed cell stents, so as to maintain the integrity of the stent. Typically, open-cell stents cannot be properly crimped back onto the balloon once expanded because non-linked struts tend to not fold back well. In contrast, a closed-cell can usually be crimped back after being expanded. For example, if Medtronic Inc.'s ENDEAVOR® or RESOLUTE INTEGRITY® open-cell stents are used, the stent may be taken off the balloon without inflating the balloon catheter. Alternatively, a closed-cell stent such as Cordis Corporation's CYPHER® stent may be taken off the balloon by first inflating the balloon and then expanding the stent.

The dual balloon and other configurations of open-celled stents as described herein may be pre-manufactured. This would ensure that the open cell stents are not damaged by manual handling of the stents.

This stent configuration (i.e., a balloon catheter, a stent, and a second guide-wire positioned between the balloon and the stent) may be constructed by the operator or may be pre-built by a manufacturer. An advantage of this configuration is that its cross-section profile may be the lowest, especially if the device is pre-built by the manufacturer, due to the missing side lumen. However, the same configuration may require above-average operator skill to maneuver the second wire trapped under the stent into the side branch. Specifically, the entire balloon-stent-second-wire device may have to be maneuvered into the main branch and turned so that the second wire enters the second side branch. In some cases, to alleviate these concerns, a spring-coiled tip wire (e.g., Boston Scientific Corp.'s CHOICE® Floppy Guide Wire or the Zinger® Support Guidewire by Medtronic) may be used as the second wire under the stent and the tip may be steered into the second side branch, even though the spring coil is under the stent, because the distal wire tip is connected to the steel core of the wire under the spring coils.

Again, in the case of the off-label use of a closed-cell stent, for example, a traditional stent balloon (e.g., the CYPHER® stent) may be inflated outside the body and the stent expanded. A secondary wire (e.g., a 0.014 spring tip wire because the internal stent wire is attached to the tip and can rotate the tip even if the wire is under the crimped stent) may be introduced between the balloon and the stent struts. The stent may be re-crimped to trap the secondary wire between the stent and the balloon. In some applications, an approximately ~3-5 mm tip of the wire may be kept curved beyond the stent. Additionally, a 0.014 guide wire may be introduced to the main (or only) lumen to prevent damage to this channel when re-crimping the stent. As described above, the stent may be positioned forward onto the distal shoulder of the balloon, usually at the distal edge of the distal balloon marker on the shaft. The stent may be then re-crimped (e.g., manually by the operator's fingers), and a #2.0 silk or the like may be wrapped around the stent and further crimped manually. A 6F sheath may also be cut into approximately ~1.5-2.5 inches, split, and placed on the shaft of the balloon with the second wire in it. The proximal side of this piece of the sheath may be beveled and used to introduce the stent through the valve of a Touhy borst adapter or another medical apparatus used for attaching catheters to other devices. The stent may be loaded on the wire that is main branch of the bifurcation. As the stent is advanced, the secondary wire may be manipulated so that it enters the side branch of the bifurcation. Again, the stent may advance until it stops naturally at the carina. After the stent is deployed at the carina and the balloon is being deflated, the side branch wire may be advanced into the side branch, and the process may continue similarly as otherwise described herein.

In the case of the off-label use of an open-cell stent, an operator may receive an assembled device including a balloon catheter and the open-cell stent. As before, the balloon catheter may be a single-lumen catheter—i.e., configured to accept only one guide wire. However, rather than inflating the balloon to expand the stent, the operator may slide the stent off of the balloon to remove it from the assembly. The stent may be loosened off the balloon by rocking the proximal and distal portions of the balloon shaft within the stent in multiple directions. This expands the stent minimally to get it off the balloon. For example, in some cases an approximately ~8-9 mm stent may be used for this purpose. Then, a second guide wire may be added between an inner surface of the stent and an outer surface of the balloon catheter, and the stent may be slid back over the catheter, thus trapping the second guide wire between the stent and the catheter. The distal edge of the stent in the assembled device may be at the distal shoulder region of the balloon. The stent may be re-crimped manually, for example, with a #2 silk thread similarly as described for the closed-cell stent above.

In some situations, when there is a stent with a second wire under the stent, either assembled at the time of the case with available materials (as described above) or pre-manufactured as described herein, an introducer device may be used to get the stent-wire configuration across a hemostasis valve without damaging or changing the shape of the second guide wire tip protruding from the distal edge of the stent. Such an introducer may be manufactured in vitro, for example, by cutting an appropriate length of a #6 French sheath as described above.

FIG. 13A illustrates open-cell stent 1305 that may be used to assemble a bifurcation delivery device following the operations described in connection with FIG. 14. Particularly, open-cell stent 1305 with a crown of struts 1330 may have one or more struts unattached to the adjacent crown of struts, thus creating a few struts 1310 that are interconnected. In this case, cells 1340 are considered to be open—although, typically, one of every 3-6 cells may be connected to each other.

Figure 15:
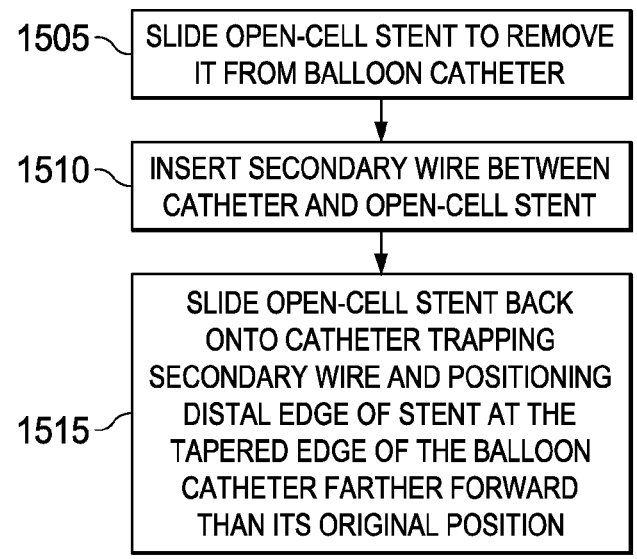
FIG. 15 is a flowchart of a bifurcation stent delivery device assembly using a single-lumen catheter with an open-cell stent according to some embodiments.

FIG. 13B shows closed-cell stent 1315, which may be used following the operations described in FIG. 15. In contrast with open-cell stent 1305, every crown of struts 1335 of closed-cell stent 1315 is connected to the adjacent crown of struts 1335, thus creating all closed cells 1320.

FIG. 13C shows an example of a bifurcation stent delivery device employing a single-lumen catheter, as described above. Device 1300 is similar to device 400C shown in FIG. 4C, but without second lumen 244. In device 1300, side guide wire 1301 is crimped between stent 1302 and catheter 1303. Although stent 1302 is illustrated as a closed-cell stent (e.g., as in FIG. 13B), an open-cell stent may also be used (e.g., as in FIG. 13A). In situations where the device is assembled by an operator in an "off-label" procedure (i.e., as opposed to pre-built by a manufacturer), the methods depicted in FIGS. 14 and 15 may be employed. Main guide wire 1304 is positioned in the vessel across the bifurcation and into a first branch. Device 1300 may be advanced along main guide wire 1304 into the vessel toward the bifurcation. Side guide wire section 1301A will be guided into the second branch as device 1300 approaches the bifurcation. Wire section 1301A may be curved to assist in "catching" the second branch. This will stop the balloon 1303 and stent 1302 adjacent to the carina of the bifurcation. The stent may then be deployed and splayed across the bifurcation as described above.

Figure 14:
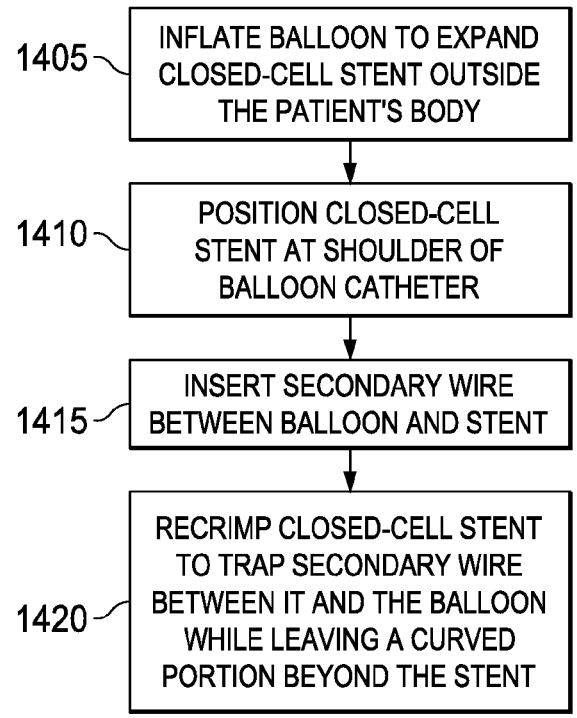
FIG. 14 is a flowchart of a bifurcation stent delivery device assembly using a single-lumen catheter with a closed-cell stent according to some embodiments.

Turning now to FIG. 14, a flowchart of a bifurcation stent delivery device assembly using a single-lumen catheter with a closed-cell stent (e.g., in FIG. 13B) is depicted according to some embodiments. At block 1405, the user may inflate the balloon to expand the stent outside the patient's body. At block 1410, a user may position a stent at a forward shoulder of a balloon catheter having a single lumen. Positioning the stent at the forward shoulder of the lumen will help to deploy the stent right at the carina of the bifurcation. At block 1415, the user may insert a secondary wire between the balloon and the stent. Then, at block 1420, the user may re-crimp the stent to trap the secondary wire between the stent and the balloon while leaving a curved portion beyond the stent. The curved portion will be directed into a side branch at the bifurcation to help position the stent at the carina.

The technique shown in FIG. 14 is particularly suitable for use with closed-cell stents, where the stent is amenable to being expanded and re-crimped, thus returning to its original configuration. As the inventor hereof has recognized, in the case of open-cell stents, it may not be possible to return the stent to its original form after its initial expansion. Nonetheless, it has been determined that, with respect to pre-assembled stent delivery devices having an open-cell stent surrounding a balloon catheter, the open-cell stent in certain types of stents, may be removed from the assembly without causing damage to the stent or to the catheter without inflating the stent.

Accordingly, FIG. 15 is a flowchart of a bifurcation stent delivery device assembly using a single-lumen catheter with an open-cell stent according to some embodiments. At block 1505, the user or operator may receive the pre-assembled delivery device and may slide the open-cell stent off of the catheter to remove it from the assembly. In some cases, this operation may require that the user apply some amount of manipulation to loosen the stent and use some amount of gentle force to get the stent off the balloon. At block 1510, the operator may insert a secondary guide wire between the balloon and the stent. Then, at block 1515, the user may slide the stent back over the balloon catheter, thus trapping the secondary guide wire between the stent and the balloon while positioning the distal edge of the stent at the tapered edge of the balloon, typically farther forward that its original position in the assembly.

In some cases, the pre-assembled device may be such that the edge of the open-cell stent is positioned at the distal shoulder region of the catheter (e.g., very close to, or exactly on the tapered edge). In many applications, such repositioning of the open-cell stent may ensure that the second guide wire, now trapped between the stent and the balloon catheter, will cause a) the stent to stop at the carina of the bifurcation and b) the stent to be deployed accurately at the carina of a bifurcation during balloon expansion.

Figure 16A:
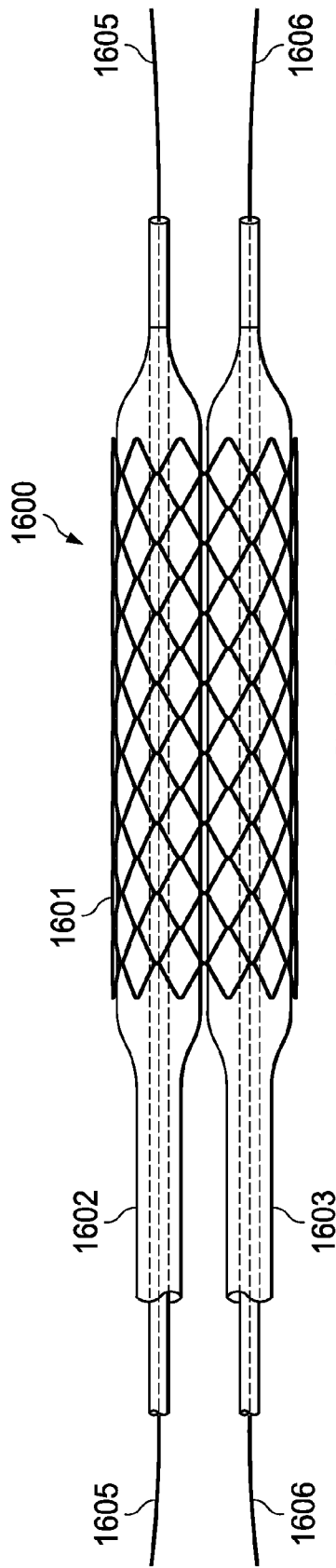
FIGS. 16A-C are diagrams of alternative delivery devices according to some embodiments.
Figure 16B:
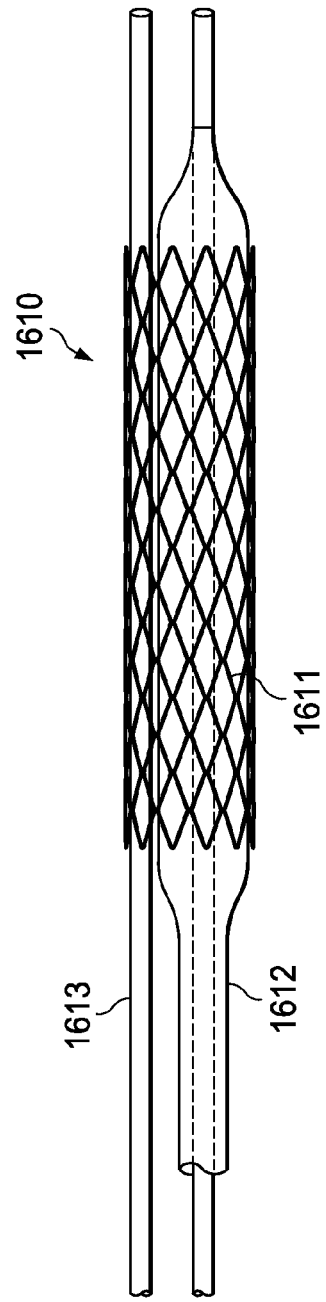
Figure 16C:
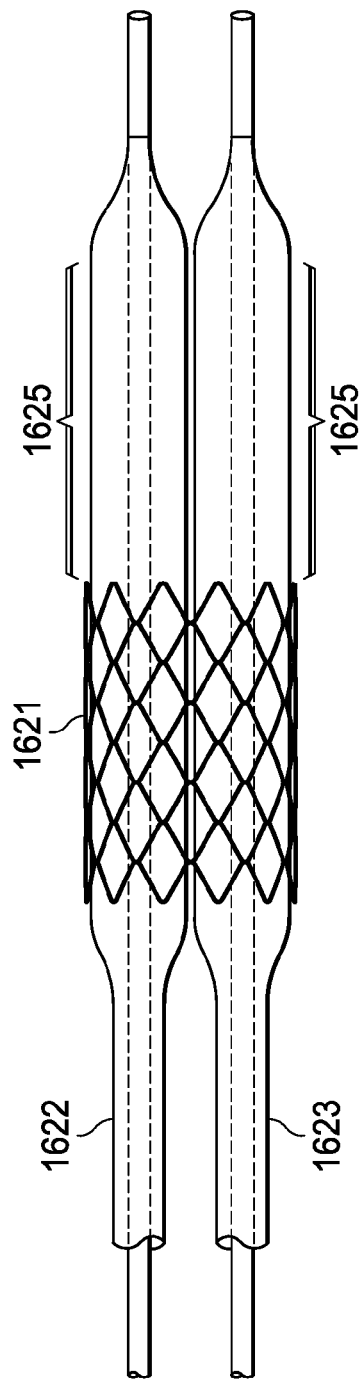

FIGS. 16A-C are diagrams of alternative delivery devices according to some embodiments. Particularly, FIG. 16A shows a dual balloon configuration 1600 with single stent 1601 crimped over two balloons 1602 and 1603. Radiopaque markers on the shaft or the stent may be used to help position the stent at the carina. In some implementations, a commercially available stent-balloon catheter may be modified by crimping stent 1601 over two parallel balloon catheters 1602 and 1603. Balloons 1602 and 1603 are sized to fit into the first and second side branches of a bifurcation. Two parallel guide wires 1605 and 1606 are first placed in the vessel and each guide wire is positioned into its own side branch of the bifurcation. Each balloon 1602, 1603 is then advanced along the guide wires 1605 and 1606 though the vessel to the bifurcation. The two balloon-stent device 1600 may stop at the carina and the stent then may be deployed at this location by inflating both the balloons at the same time. In such an embodiment, the deployment and splaying of the distal portion of the stent may occur at the same time as pre-dilatation of the stenosis in the first and second side branches. If only open-cell stents are available on the market, this dual balloon configuration may be pre-manufactured. The configuration may be used with the closed-cell Cypher stent, but this stent is currently off the market and no longer available from the manufacturer.

FIG. 16B depicts stent delivery device 1610 according to an alternative embodiment. Specifically, stent 1611 is crimped over a parallel combination of balloon catheter 1612 (for a first guide wire) and a long tube catheter 1613 with an approximately 0.014-inch wire lumen (for a second guide wire). Device 1610 may also include markers (not shown) on the shaft of the stent itself to assist in positioning the device. The embodiment of device 1610 with catheter 1613 may facilitate accurate delivery at the carina while maintaining dual side branch access through the stent lumen.

FIG. 16C depicts another embodiment of a stent delivery device. Stent 1621 is crimped over balloon catheters 1622 and 1623. The catheters have inflation balloon sections that are longer than stent 1621. As a result, sections 1625 on each balloon 1622, 1623 extend beyond the distal edge of stent 1621. This configuration may be useful, for example, to dilate each side branch 120A and 120B (FIG. 10) of the bifurcation when stent 1621 is deployed. This would prepare the side branches for a subsequent kissing stenting operation. Additionally, the inflation of segments 1625 in different side branches would cause stent 1621 to be splayed across the bifurcation with the first inflation itself. This embodiment may make it easier to splay stent 1621 in order to achieve the configuration depicted in of FIG. 10 and FIG. 11, for example.

Figure 17A:
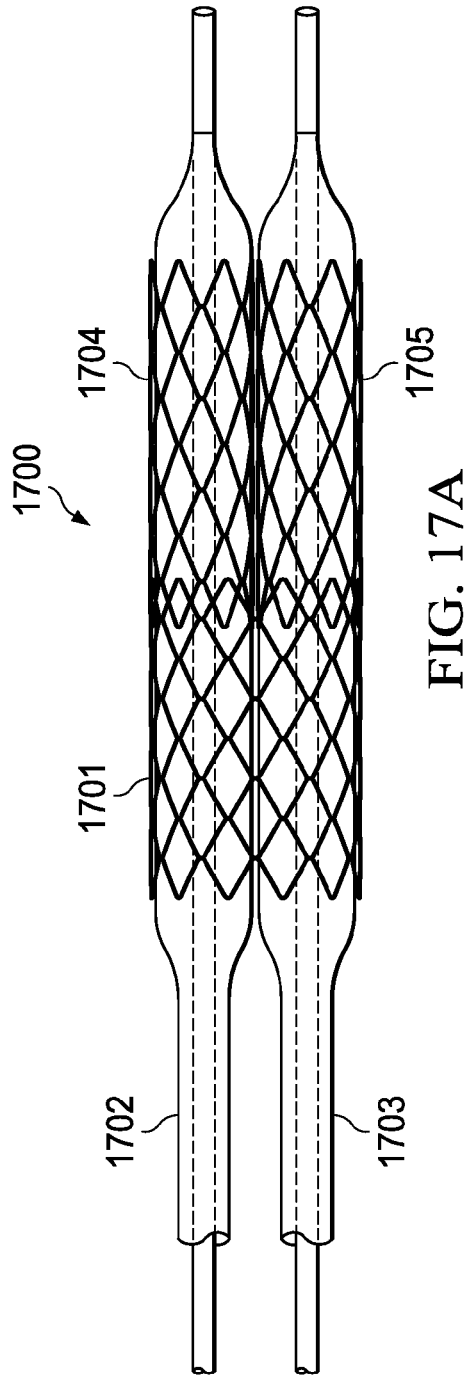
FIGS. 17A-B illustrate a three-stent delivery device according to an alternative embodiment.

FIG. 17A illustrates a three-stent delivery device 1700 according to another alternative embodiment. A stent 1704 is positioned on balloon 1702 and stent 1705 is positioned on balloon 1703. Thereafter stent 1701 is positioned around both the balloon catheters 1702 and 1703, with the distal end of the stent overlapping the stents 1704 and 1705. This configuration allows for the simultaneous deployment of stent 1701 in the main vessel before a bifurcation and deployment of stents 1704 and 1705 in separate side branches.

Figure 17B:
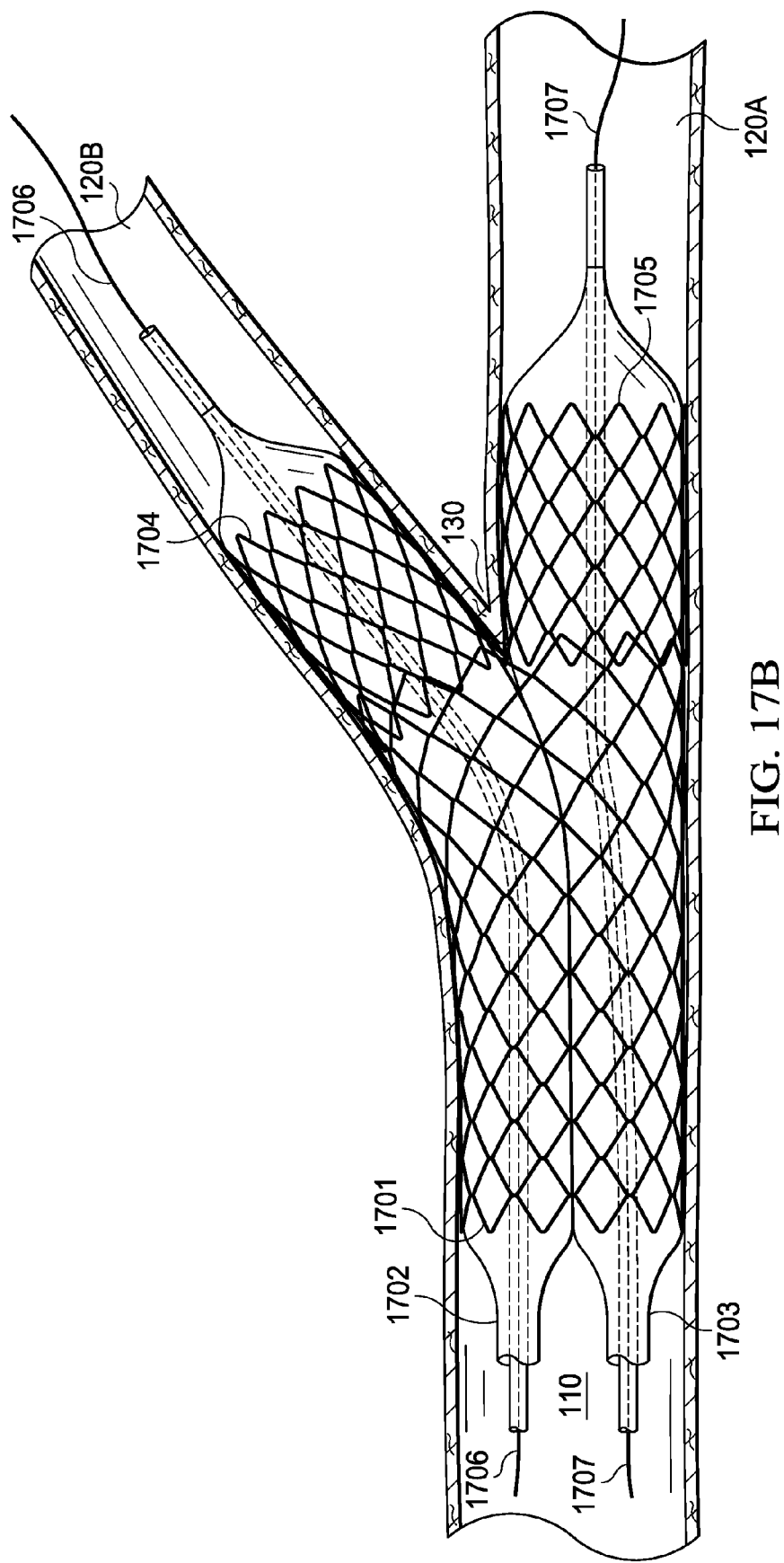

FIG. 17B illustrates device 1700 deployed at a bifurcation. First, guide wires 1706, 1707 are positioned though main vessel 110 and into separate side branches 120A, 120B. Then, device 1700 is advanced along the guide wires with balloon catheter 1702 traveling along guide wire 1706 and balloon catheter 1703 traveling along guide wire 1707. As device 1700 approaches the bifurcation, the balloons are directed into separate side branches. The device will stop moving into the vessel when the balloon segments covered by stents 1704 and 1705 have entered the side branches. Stent 1701 cannot move into the side branches, but will be stopped at carina 130. Once the device 1700 is positioned with stent 1701 at the carina in this manner, the balloons 1702, 1703 may be inflated as illustrated in FIG. 17B. This inflation will simultaneously deploy stent 1701 in the main vessel proximal to carina 130 and stents 1704, 1705 in the side branches distal to carina 130. Additionally, device 1700 performs the kissing balloon techniques when it is inflated, which splays stent 1701 across the bifurcation.

As a person of ordinary skill in the art will recognize in light of this disclosure, one or more of the numerous embodiments described herein may provide one or more advantages over known stent deployment techniques. For example, some of these embodiments may prevent guide wires from becoming tangled. In some cases, access to a side branch may be maintained using the second guide wire when deploying a stent in the main vessel. Furthermore, the wire going into the side branches may be maintained within the lumen of the stent, rather than through the stent struts. One or more of the techniques disclosed herein may also guarantee the exact location of the stent at the carina, which makes it less likely that areas of the bifurcation lesion will remain uncovered by stents after treatment.

Moreover, in contrast with existing devices currently used to treat bifurcation lesions, one or more of the devices disclosed herein may be manufactured with a low or small profile, may be easy to maneuver, and may therefore be particularly well suited for the treatment of coronary arteries, which are typically small in diameter (although it may also be used in any bifurcation lesion). In some devices, the side lumen may ensure access to the side branch of the bifurcation. Further, in some cases, the side guide wire may help place the main stent exactly at the carina. Because in embodiments where the bare wire is trapped under the stent the side guide wire is generally unable to move within the lumen, a 'V' shape may be created between the guide wire and the balloon catheter of the main branch stent. As the device advances with the side wire in the side branch and the main wire in the main branch, it may stop at the vertex of bifurcation. As such, one or more of the techniques described herein may guarantee precise placement of a stent at the carina with any amount of plaque buildup in the arteries, and while ensuring there is full coverage of the bifurcation. Under fluoroscopy in two dimensions, it is often very difficult to identify the precise location of the carina in two dimensions because of variable side branch vessel overlap. Hence the particular suitability of certain of these techniques and innovations to accurately place stents at bifurcations in coronary, peripheral vascular, venous or other anatomical locations.

In some cases, the stent delivery systems and methods described herein may provide a 100% or near 100% apposition or coverage of the bifurcation lesion by the stent struts, thereby eliminating a limitation of present day stenting of such lesions. In a typical scenario, 100% coverage of the lesion may be a particularly critical issue with local lesion drug delivery by drug eluting stents to prevent restenosis. In addition, 100% or near 100% stent apposition to the bifurcation lesion ensures that luminal access to each branch is wide open—that is, stent struts do not protrude into the lumen and a true pantaloons configuration may be obtained. This method of stenting may therefore eliminate or otherwise reduce the risk of stent thrombosis due to stent struts that are not opposed to the wall of the vessel. Furthermore, in the case of restenosis or new lesions developing downstream to the bifurcation, normal anatomical access allows subsequent operators to cross through the bifurcation with wires, balloons and stents without any metallic luminal obstacles caused by struts not in apposition to the walls of the bifurcation.

In some cases, the stent delivery systems and methods described herein may also prevent the carina of the bifurcation from being shifted from its anatomical location. This may be guaranteed by deflating the kissing balloons together at the same inflation pressures. The stent in the main vessel may be accurately delivered at the carina by making sure that the distal end of the stent is positioned forward on the shoulder or distal taper of the deploying balloon than is the case with more conventional stents. In addition, problems of plaque shifting are also eliminated or otherwise reduced. In various implementations, the two wires in each lumen may always be within the lumen of the stents and do not at any time go through stent struts.

Certain conventional balloon and stent profiles are small enough to utilize certain of the stent delivery techniques described herein, for instance, through an 8F (crossing profile of the guiding catheter) system. For example, the closed-cell design of the CYPHER® stent is particularly suitable for this method because it can be re-crimped after expanding it outside the patient's body. Other open cell stents such as, for example, the ENDEAVOR®, or the RESOLUTE INTEGRITY® may be loosened and removed from the balloon without expanding the stent. Also conventional stents, wires, and materials may be used to reconfigure a stent for delivery at the bifurcation (i.e., off-FDA label utilization of these stents). While such an off-label technique may require a higher level of operator expertise for reconfiguration of the stent for the bifurcation, after the initial learning curve is overcome, such a method is also very feasible.

With one or more of the innovations described herein, stent delivery systems can be created to make the delivery operator friendly and achieve routine use for bifurcation stenting. Additional innovations described herein may be used to accurately deliver a stent at a trifurcation, for example, a left-main trifurcation into the left anterior descending, ramus intermedius and circumflex arteries. Yet additional innovations may accurately deliver stents beyond the carina without jailing a side branch. This may be utilized in other non-bifurcation lesion situations where stenting is required in the main vessel but the stent needs to be delivered without jailing a side branch, while maintaining access to the branch in case the carina is shifted.

As such, in various embodiments, the stent delivery systems and methods described herein may be particularly useful for use with patients who cannot undergo bypass surgery safely. Moreover, one or more of these techniques may be safely used in patients with "complex" bifurcation lesions, thus making complex bifurcation operations a matter of routine; thus helping decrease the need for such surgery.

The various systems and methods illustrated in the figures and described herein represent example embodiments of systems and methods for deploying stents within bifurcated blood vessels. The order in which each operation of a given method is performed may be changed, and various elements of the systems or devices illustrated herein may be added, reordered, combined, omitted, modified, etc. Various modifications and changes may be made as would be clear to a person of ordinary skill in the art having the benefit of this specification. It is intended that the invention(s) described herein embrace all such modifications and changes and, accordingly, the above description should be regarded in an illustrative rather than a restrictive sense.

The invention claimed is:

1. A method of configuring a stent delivery device, the method comprising:
   receiving an assembled stent delivery device including a balloon catheter and a stent crimped over at least a portion of the balloon catheter, the balloon catheter consisting of a single lumen, the single lumen configured to accept a first guide wire;
   removing the stent from the balloon catheter;
   adding a second guide wire between an inner surface of the stent and an outer surface of the balloon catheter after having removed the stent and while a distal end of the second guide wire is outside of a patient's body; and re-crimping the stent over the balloon catheter after having added the second guide wire such that the second guide wire is in direct physical contact between the inner surface of the stent and the outer surface of the balloon catheter.

2. The method of claim 1, wherein re-crimping the stent over the balloon catheter includes positioning a distal edge of the stent along a proximate edge of a distal tapered portion of the balloon catheter.

3. The method of claim 1, wherein the stent is an open-cell stent.

4. The method of claim 3, wherein removing the stent from the balloon catheter includes removing the stent without inflating the balloon catheter.

5. The method of claim 1, further comprising:
advancing the balloon catheter within a vessel using the first guide wire until the balloon catheter stops at a carina of a bifurcation due, at least in part, to the carina contacting the second guide wire;
deploying the stent straddling a first side branch and a second side branch of the bifurcation; and
splaying a distal end of the stent with a kissing balloon technique.

6. The method of claim 3, further comprising:
delivering a second stent to the first side branch of the bifurcation using the first guide wire; and
delivering a third stent to the second branch of the bifurcation using the second guide wire.

\* \* \* \* \*